(12) United States Patent
Angold et al.

(10) Patent No.: US 8,057,410 B2
(45) Date of Patent: Nov. 15, 2011

(54) SEMI-POWERED LOWER EXTREMITY EXOSKELETON

(75) Inventors: Russdon Angold, American Canyon, CA (US); Nathan H. Harding, Oakland, CA (US); Homayoon Kazerooni, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 1263 days.

(21) Appl. No.: 11/404,719

(22) Filed: Apr. 13, 2006

(65) Prior Publication Data

US 2007/0056592 A1    Mar. 15, 2007

Related U.S. Application Data

(60) Provisional application No. 60/671,348, filed on Apr. 13, 2005.

(51) Int. Cl.
*A61H 3/00* (2006.01)
(52) U.S. Cl. .............................................. 601/5; 601/35
(58) Field of Classification Search ................ 601/5, 23, 601/24, 26, 33, 34, 35; 600/587, 595; 602/23, 602/26
See application file for complete search history.

(56) References Cited

U.S. PATENT DOCUMENTS

| 406,328 A | 7/1889 | Yagn |
|---|---|---|
| 420,178 A | 1/1890 | Yagn |
| 420,179 A | 1/1890 | Yagn |

(Continued)

FOREIGN PATENT DOCUMENTS

CN    1586434    3/2005

(Continued)

OTHER PUBLICATIONS

International Search Report and Written Opinion mailed Aug. 15, 2007, for PCT Application No. PCT/US06/14227 filed Apr. 13, 2006, 13 pages.

(Continued)

*Primary Examiner* — Danton DeMille
(74) *Attorney, Agent, or Firm* — Diederiks & Whitelaw PLC

(57) ABSTRACT

The lower extremity exoskeleton comprises two leg supports connectable to person's lower limbs and configured to rest on the ground during their stance phase. Each leg support comprises a thigh link and a shank link; a knee joint configured to allow flexion and extension between the shank link and the thigh link. The lower extremity exoskeleton further comprises an exoskeleton trunk connectable to the person's upper body. The exoskeleton trunk is connectable to the thigh links of the leg supports allowing for the flexion and extension between the leg supports and the exoskeleton trunk. Two torque generators are coupled to each of the knee joints. A power unit, capable of providing power, is coupled to the torque generators. In operation when a leg support is in a stance phase and climbing a slope or stairs, the power unit injects power into the respective torque generator thereby extending the respective knee angle. When a leg support is in stance phase and not climbing a slope or stairs, the power unit does not inject any power to the respective torque generator, but without dissipating any stored power in said power unit, it forces the torque generator to resist flexion of the respective knee joint. When a leg support is in a swing phase, the power unit does not inject any power to the respective torque generator, but without dissipating any stored power in said power unit, it forces the torque generator to minimize its resistance to knee flexion and extension.

79 Claims, 30 Drawing Sheets

U.S. PATENT DOCUMENTS

| | | | |
|---|---|---|---|
| 440,684 | A | 11/1890 | Yagn |
| 539,872 | A | 5/1895 | Kheiralla |
| 807,908 | A | 12/1905 | Bradstreet |
| 979,243 | A | 12/1910 | Anderson |
| 1,308,675 | A | 7/1919 | Kelly |
| 4,647,004 | A | 3/1987 | Bihlmaier |
| 4,872,665 | A * | 10/1989 | Chareire ........................ 482/51 |
| 5,020,790 | A | 6/1991 | Beard et al. |
| 5,282,460 | A * | 2/1994 | Boldt ................................ 601/5 |
| 5,476,441 | A | 12/1995 | Durfee et al. |
| 5,658,242 | A | 8/1997 | McKay et al. |
| 5,662,693 | A | 9/1997 | Johnson et al. |
| 5,961,476 | A | 10/1999 | Betto et al. |
| 6,422,329 | B1 | 7/2002 | Kazerooni et al. |
| 6,500,210 | B1 | 12/2002 | Sabolich et al. |
| 6,676,707 | B2 | 1/2004 | Yih et al. |
| 6,807,869 | B2 | 10/2004 | Farringdon et al. |
| 6,821,233 | B1 | 11/2004 | Colombo et al. |
| 6,966,882 | B2 | 11/2005 | Horst |
| 7,048,707 | B2 | 5/2006 | Schwenn et al. |
| 7,111,704 | B2 | 9/2006 | Johnson |
| 7,153,242 | B2 | 12/2006 | Goffer |
| 7,313,463 | B2 | 12/2007 | Herr et al. |
| 7,445,606 | B2 * | 11/2008 | Rastegar et al. .................. 601/5 |
| 2003/0018283 | A1 * | 1/2003 | Dariush ....................... 600/595 |
| 2004/0106881 | A1 * | 6/2004 | McBean et al. ................... 601/5 |
| 2004/0116839 | A1 | 6/2004 | Sarkodie-Gyan |
| 2004/0158175 | A1 * | 8/2004 | Ikeuchi et al. .................... 601/5 |
| 2004/0249319 | A1 * | 12/2004 | Dariush ............................ 601/5 |
| 2005/0102111 | A1 * | 5/2005 | Dariush et al. .................. 702/41 |
| 2006/0004307 | A1 * | 1/2006 | Horst ................................ 601/5 |
| 2006/0046907 | A1 | 3/2006 | Rastegar et al. |
| 2006/0249315 | A1 | 11/2006 | Herr et al. |
| 2006/0260620 | A1 | 11/2006 | Kazerooni et al. |
| 2007/0043449 | A1 | 2/2007 | Herr et al. |
| 2007/0123997 | A1 | 5/2007 | Herr et al. |
| 2007/0162152 | A1 | 7/2007 | Herr et al. |
| 2008/0154165 | A1 | 6/2008 | Ashihara et al. |

FOREIGN PATENT DOCUMENTS

| | | |
|---|---|---|
| CN | 101094640 | 12/2007 |
| EP | 1260201 | 11/2002 |
| WO | WO-2007/016781 | 2/2007 |

OTHER PUBLICATIONS

International Search Report and Written Opinion mailed Aug. 7, 2007, for PCT Application No. PCT/US06/01981 filed Jan. 18, 2006, 11 pages.

International Search Report and Written Opinion mailed Jan. 28, 2008, for PCT Application No. PCT/US07/06122 filed Mar. 9, 2007, 12 pages.

Racine, J.C. (2003). "Control of a Lower Exoskeleton for Human Performance Amplification," PhD Thesis, UC Berkeley, pp. 1-340.

Johnson, D., et al. "Development of a Mobility Assist for the Paralyzed, Amputee, and Spastic Patient." Proceedings of the Fifteenth Southern Biomedical Engineering Conference, IEEE, pp. 67-70, Dayton, Ohio, Mar. 1996.

Yamamoto, K., et al. "Development of Power Assisting Suit for Assisting Nurse Labor." JSME International Journal Series C., vol. 45, No. 3, Sep. 2002.

Yamamoto, K., et al. "Development of Power Assisting Suit (Miniaturization of Supply System to Realize Wearable Suit)." JSME International Journal Series C., vol. 46, No. 3, Sep. 2003.

Vukobratovic, M., et al. "Development of Active Anthropomorphic Exoskeletons." Medical and Biological Engineering, pp. 66-80, Jan. 1974.

Misuraca, J., et al. "Lower Limb Human Muscle Enhancer." Proceedings of the Symposium on Advances in Robot Dynamics and Control, ASME International Mechanical Engineering Congress and Exposition (IMECE), New York, New York, Nov. 2001.

Belforte, G., et al. "Pneumatic Active Gait Orthosis." Mechatronics, vol. 11, No. 3, pp. 301-323, Apr. 2001.

Kasaoka, K., et al. "Predictive Control Estimating Operator's Intention for Stepping-up Motion by Exoskeleton Type Power Assist System HAL." Proceedings of the IEEE/RJS International Conference on Intelligent Robots and Systems (IROS), vol. 3, pp. 1578-1583, Maui, Hawaii, Nov. 2001.

Kawamoto, H., et al. "Comfortable Power Assist Control Method for Walking Aid by HAL-3." Proceedings of the IEEE International Conference on Systems, man, and Cybernetics (SMC), vol. 4, Hammamet, Tunisia, Oct. 2002.

Lee, S. et al. "Power Assist Control for Walking Aid with HAL-3 Based on EMG and Impedance Adjustment around Knee Joint." Proceedings of the IEEE/RJS International Conference on Intelligent Robots and Systems (IROS), vol. 2, pp. 1499-1504, Lausanne, Switzerland, 2002.

Kawamoto, H., et al. "Power Assist System HAL-3 for Gait Disorder Person." Lecture Notes in Computer Science (LNCS), vol. 2398, Proceedings of the Eighth International conference on Computers Helping People with Special Needs (ICCHP), pp. 196-203, Berlin, Germany, 2002.

Van Den Bogert, A. "Exotendons for Assistance of Human Locomotion." Biomedical Engineering Online, vol. 2, Oct. 2003.

Mori, Y., et al. "Development of Straight Style Transfer Equipment for Lower Limbs Disabled." Proceedings of the IEEE International Conference on Robotics and Automation (ICRA), vol. 3, pp. 2486-2491, New Orleans, Louisiana, May 2004.

Irby, S., et al. "Automatic Control Design for a Dynamic Knee-Brace System." IEEE Transactions on Rehabilitation Engineering, vol. 7, No. 2, pp. 135-139, Jun. 1999.

Ferris, D., et al. "An Ankle-foot Orthosis Powered by Artificial Muscles." Proceedings of the 25th Annual Meeting of the American Society of Biomechanics, San Diego, California, Aug. 2001.

Naruse, K., et al. "Design of Compact and Lightweight Wearable Power Assist Device." Proceedings of ASME International Mechanical Engineering Congress and Exposition (IMECE), Washington D.C., Nov. 2003.

Pratt, J., et al. "The RoboKnee: An Exoskeleton for Enhancing Strength and Endurance During Walking." Proceedings of the IEEE International Conference on robotics and Automation (ICRA), vol. 3, pp. 2430-2435, New Orleans, Louisiana, May 2004.

Morris, S., et al. "Shoe-integrated Sensor System for Wireless Gait Analysis and Real-Time Feedback." Proceedings of the Second Joint EMBS/BMES Conference, pp. 2468-2469, Houston Texas, Oct. 2002.

Harley, J.A. "Design and Construction of an Underactuated Assistive Walking Device." Graduate Thesis, UC-Berkeley Mechanical Engineering Dept., Aug. 1995.

Lim, Michael Zin Min, "An Analysis on the Performance of an Underactuated Lower Extremity Enhancer." Graduate Thesis, UC-Berkeley Mechanical Engineering Dept., 2000.

Clark, D.C. et al. "Exploratory Investigation of the Man Amplifier Concept." Technical Documentary Report No. AMRL-TDR-62-89, United States Air Force, Wright-Patterson Air Forces Base, Ohio, Aug. 1962.

"Machine Augmentation of Human Strength and Endurance: Hardiman I Prototype Project." General Electric Company, Schenectady, New York, Jul. 1969.

Makinson, B.J. "Research and Development Prototype for Machine Augmentation of Human Strength and Endurance: Hardiman I Project." General Electric Company, Schenectady, New York, May 1971.

Gilbert, K.E. "Exoskeleton Prototype Project." General Electric Company, Schenectady, New York, Oct. 1966.

Mosher, R.S. "Handyman to Hardiman." Automotive Engineering Congress, Society of Automotive Engineers, Detroit, Michigan, Jan. 1967.

Arroyo, P. "Design of a Minimally Actuated Assistive Device." Graduate Thesis, UC-Berkeley Mechanical Engineering Dept., 1998.

Rehnmark, F.L. "Dynamic Simulation and Design of a Powered Underactuated Assistive Walking Device." Graduate Thesis, UC-Berkeley Mechanical Engineering Dept., 1997.

Chu, A. "Design Overview of 1$^{st}$ Generation Exoskeleton," Master of Science Thesis, UC Berkeley, Apr. 3, 2003.

Zoss, A. "Mechanical Design Implementation of an Exoskeleton," Master of Science Thesis, UC Berkeley, Spring 2003.

U.S. Appl. No. 10/976,652, filed Oct. 29, 2004, for Kazerooni.

First Chinese Office Action dated Apr. 27, 2009, for CN Application No. 200680006514.1, filed Jan. 18, 2006. 8 pages. (English translation, 8 pages).
First Chinese Office Action dated Sep. 25, 2009, for CN Application No. 200680017031.1, filed Apr. 13, 2006, 8 pages.
U.S. Appl. No. 12/552,021, filed Sep. 1, 2009 for Herr et al.
U.S. Appl. No. 60/666,876, filed Mar. 1, 2005 for Herr et al.

Carrozza et al., *On the Design of an Exoskeleton for Neurorehabilitation: Design Rules and Preliminary Prototype*, Proceedings of the 26$^{th}$ Annual International Conference of the IEEE EMBS, vol. 4, Sep. 2005, pp. 4807-4810.

* cited by examiner

SEMI-POWERED LOWER EXTREMITY EXOSKELETON

CROSS-REFERENCE TO RELATED APPLICATIONS

This application claims the benefit of U.S. Provisional Application No. 60/671,348, titled SEMI-POWERED LOWER EXTREMITY EXOSKELETON, filed Apr. 13, 2005, the entire content of which is incorporated herein by reference.

STATEMENT REGARDING FEDERALLY SPONSORED RESEARCH OR DEVELOPMENT

This invention was made with government support under Contract No. DAAD19-01-1-0509 awarded by Defense Advanced Research Projects Agency (DARPA). The government has certain rights in the invention.

BACKGROUND

1. Field

The present invention relates generally to the field of lower extremity exoskeletons and more specifically to the field of semi-powered lower extremity exoskeletons.

2. Related Art

In a wide variety of situations, people of ordinary ability are often frustrated in attempting to carry excessively heavy or bulky objects while walking on slopes and stairs. Some people cannot even carry their own weights without becoming tired quickly or injured. Opportunities exist, therefore, to provide a compact, easy-to-operate, fast, and general purpose device to carry load while the device is being worn by a person.

SUMMARY

The opportunities described above are addressed in several embodiments of a lower extremity exoskeleton, wearable by a person. The lower extremity exoskeleton comprises two leg supports connectable to person's lower limbs and configured to rest on the ground during their stance phase. Each leg support comprises a thigh link and a shank link; a knee joint configured to allow flexion and extension between the shank link and the thigh link. The lower extremity exoskeleton further comprises an exoskeleton trunk connectable to the person's upper body. The exoskeleton trunk is connectable to the thigh links of the leg supports allowing for the flexion and extension between the leg supports and the exoskeleton trunk. Two torque generators are coupled to each of the knee joints. A power unit, capable of providing power, is coupled to the torque generators. In operation when a leg support is in a stance phase and climbing a slope or stairs, the power unit injects power into the respective torque generator thereby extending the respective knee angle. When a leg support is in stance phase and not climbing a slope or stairs, the power unit does not inject any power to the respective torque generator, but without dissipating any stored power in said power unit, it forces the torque generator to resist flexion of the respective knee joint. When a leg support is in a swing phase, the power unit does not inject any power to the respective torque generator, but without dissipating any stored power in said power unit, it forces the torque generator to minimize its resistance to knee flexion and extension.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
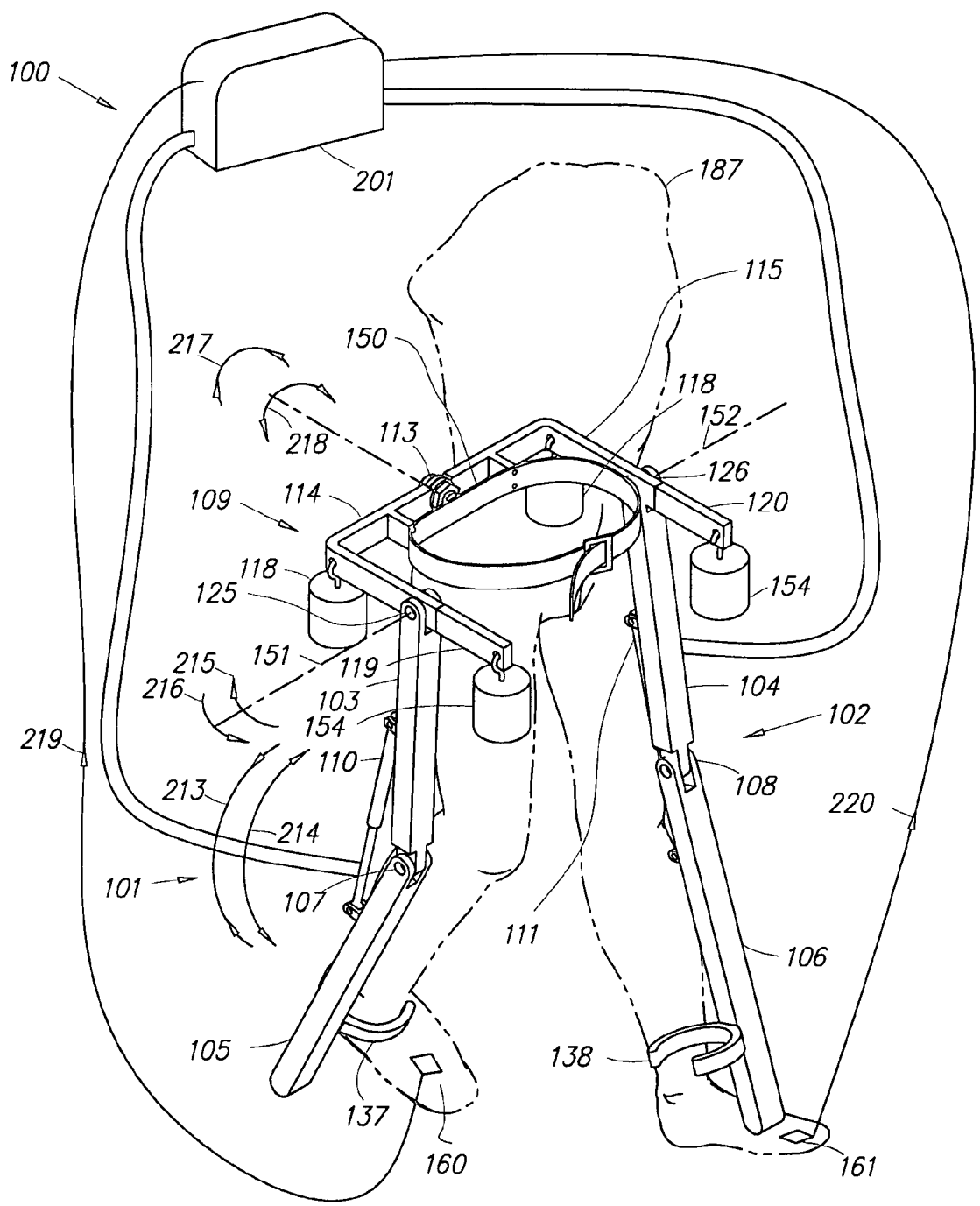
FIG. 1 is a front view perspective drawing in accordance with an embodiment of the present invention.
Figure 2:
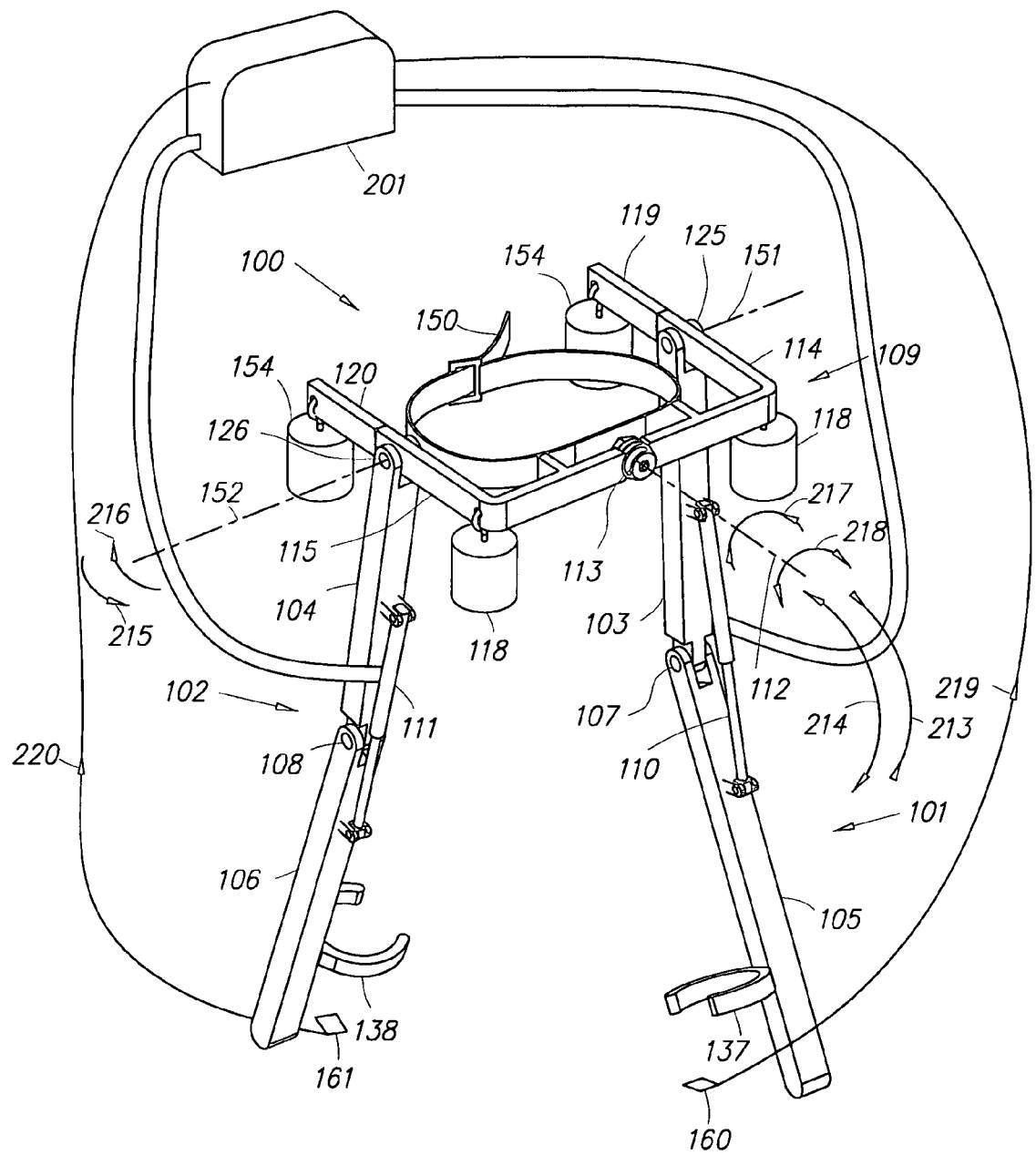
FIG. 2 is a rear view perspective drawing of the embodiment of FIG. 1.

In accordance with an embodiment of the present invention, FIG. 1 and FIG. 2 are perspective drawings illustrating a lower extremity exoskeleton 100 wearable by a person 187. Lower extremity exoskeleton 100 comprises two leg supports 101 and 102, which are configured to be connectable to the person's lower limbs and configured to rest on the ground during their stance phase. The leg supports comprise thigh links 103 and 104 and shank links 105 and 106. Two knee joints 107 and 108 are configured to allow flexion and extension between the shank and thigh of the leg supports (shown by arrows 213 and 214 respectively). Lower extremity exoskeleton 100 further comprises an exoskeleton trunk 109. Exoskeleton trunk 109, among other components, comprises a human interface device 150. Exoskeleton trunk 109 is configurable to be coupled to the person's upper body through human interface device 150. The person's upper body means any location above the thighs. Exoskeleton trunk 109 is rotatably connectable to thigh links 103 and 104 of leg supports 101 and 102 at hip flexion-extension joints 125 and 126, allowing for the hip flexion and extension rotations (shown by arrows 215 and 216 respectively) of leg supports 101 and 102 about hip flexion-extension axes 151 and 152 respectively.

Two torque generators 110 and 111 are coupled to knee joints 107 and 108. A power unit 201, capable of providing power, is coupled to torque generators 110 and 111, and is configured to operate in at least two modes for each torque generator 110 and 111. In operation, when power unit 201 operates in its first mode with respect to torque generator 110, power unit 201 injects power into torque generator 110 to extend the knee angle of leg support 101, which is defined between shank link 105 and thigh link 103 of the leg support 101. When power unit 201 operates in its second mode with respect to torque generator 110, the energy required for the flexion and extension between shank link 105 and thigh link 103 of leg support 101 over a cyclic knee motion is provided by person 187 but power unit 201 causes torque generator 110 to resist flexion. The same operation is true for torque generator 111. When power unit 201 operates in its first mode with respect to torque generator 111, power unit 201 injects power into torque generator 111 to extend knee angle of leg support 102. When power unit 201 operates in its second mode with respect to torque generator 111, the energy required for the flexion and extension between shank link 106 and thigh link 104 of leg support 102 over a cyclic knee motion is provided by person 187 but power unit 201 causes torque generator 111 to resist flexion.

A cyclic knee motion here is defined as a motion where the initial and the final configurations of a shank link (105 or 106) and its corresponding thigh link (103 or 104) with respect to each other are nearly identical. In particular when a leg support is in a swing phase, a cyclic knee motion is a motion where the leg support is not in contact with the ground and the initial and the final configurations of the corresponding shank link and thigh link with respect to each other are nearly identical. Likewise, when a leg support is in a stance phase, a cyclic knee motion is a motion where the leg support is in contact with the ground and the initial and the final configurations of the corresponding shank link and thigh link with respect to each other are nearly identical.

In some embodiments, power unit 201 further operates in a third mode for each torque generators 110 and 111. In operation, when power unit 201 operates in its third mode with respect to torque generator 110, the energy required for the flexion and extension between shank link 105 and thigh link 103 of leg support 101 over a cyclic knee motion is provided by person 187, and power unit 201 causes torque generator 110 to minimize its resistance to knee flexion and extension. Similarly when power unit 201 operates in its third mode with respect to torque generator 111, the energy required for the flexion and extension between the shank link 106 and thigh link 104 of leg support 102 over a cyclic knee motion is provided by person 187, and power unit 201 causes torque generator 111 to minimize its resistance to knee flexion and extension.

In some embodiments, as shown in FIG. 1, lower extremity exoskeleton 100 comprises at least one foot sensor per leg support. Leg support 101 includes foot sensor 160, which produces a stance signal 219 representing the force on the bottom of wearer's corresponding foot. Similarly leg support 102 includes foot sensor 161, which produces a stance signal 220 representing the force on the bottom of the other wearer's foot. Power unit 201 controls torque generators 110 and 111 as a function of stance signals 219 and 220. Stance signals 219 and 220 detect if the wearer's leg is in stance phase or in a swing phase. In some embodiments of foot sensors, stance signals 219 and 220 represent the magnitude of the force on the bottom of wearer's feet. During swing phase, stance signals 219 and 220 will detect small or zero magnitude for the force on the bottom of the wearer's feet.

Figure 20:
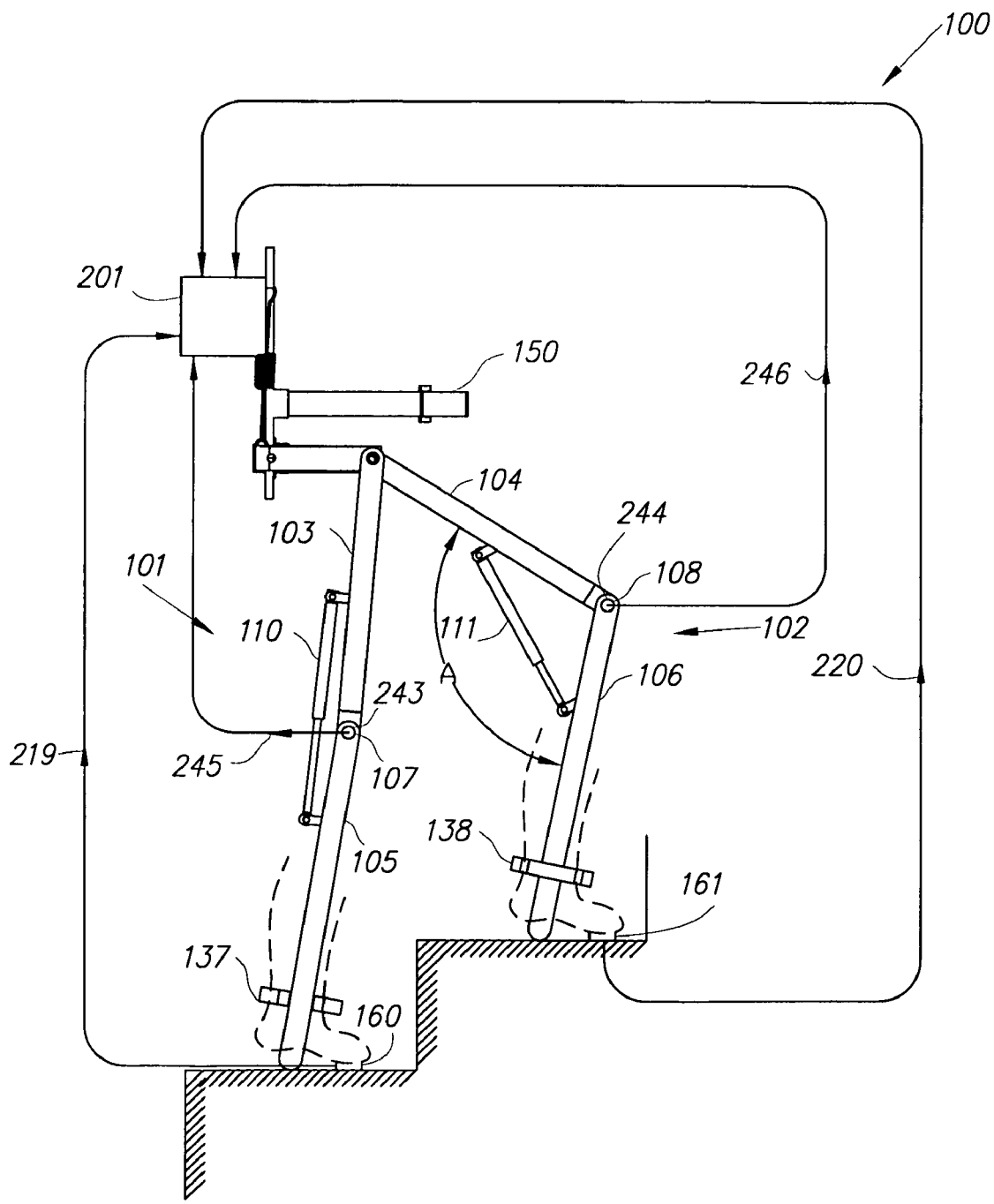
FIG. 20 is a drawing in accordance with an embodiment of the invention.

In some embodiments, as shown in FIG. 20, lower extremity exoskeleton 100 includes at least one angle sensor per leg support. Leg support 101 comprises an angle sensor 243 which produces an angle signal 245 representing the angle of knee joint 107. Similarly leg support 102 comprises an angle sensor 244 which produces an angle signal 246 representing the angle of knee joint 108. Power unit 201 controls torque generators 110 and 111 as a function of angle signals 245 and 246. Angle signals 245 and 246 detect if leg supports 101 and 102 are postured (i.e., bent) to climb stairs or a slope. In some embodiments of angle sensors, angle signals 245 and 246 represent the magnitude of the joint angles for knee joints 107 and 108.

In some embodiments, power unit 201 operates in its first mode with respect to torque generator 110, when stance signal 219 indicates the presence of a force on the bottom of corresponding human foot (i.e., leg support 101 is in a stance phase) and angle signal 245 indicates that leg support 101 is either bent or postured to climb stairs or a slope. The same is also true for torque generator 111. Power unit 201 operates in its first mode with respect to torque generator 111, when stance signal 220 indicates the presence of a force on the bottom of corresponding human foot (i.e., leg support 102 is in a stance phase) and angle signal 246 indicates that leg support 102 is either bent or postured to climb stairs or a slope. Throughout this application, climbing stairs and slopes are detected when the knee joint angle (shown as the angle "A" for knee joint 108 in FIG. 20) is bent or becomes smaller than a preset value at the beginning of the stance phase for a leg. In one embodiment, the preset value was chosen to be 135°. In another embodiment the preset value was chosen to be 165°.

In some embodiments, power unit 201 operates in the second mode with respect to torque generator 110, when stance signal 219 indicates the presence of a force on the bottom of corresponding human foot (i.e., leg support 101 is in a stance phase) and angle sensor 245 detects that leg support 101 is neither bent nor postured to climb stairs or a slope. The same is true for torque generator 111. Power unit 201 operates in second mode with respect to torque generator 111, when stance signal 220 indicates the presence of a force on the bottom of corresponding human foot (i.e., leg support 102 is in a stance phase) and angle signal 246 indicates that leg support 102 is neither bent nor postured to climb stairs or a slope.

In some embodiments, power unit 201 operates in the third mode with respect to torque generator 110, when stance signal 219 detects that leg support 101 is in a swing phase. The same is true for torque generators 111. Power unit 201 operates in third mode with respect to torque generator 111, when stance signal 220 detects that leg support 102 is in a swing phase.

In summary, power unit 201 is configurable to inject power into torque generators 110 and 111 during the stance phase of leg supports 101 and 102 and when they are bent or postured to climb stairs or slopes. To save power, during the stance phase of a leg support when it is not bent or postured to climb stairs or slopes, power unit 201 is configurable such that the energy required for the flexion and extension between the shank link and the thigh link of a leg support over a cyclic knee motion can be provided by the person. To save even more power, during the swing phase of a leg support, power unit 201 is configurable such that the energy required for the flexion and extension between the shank link and the thigh link of a leg support over a cyclic knee motion can be provided by the person. Although throughout this application we refer to "climbing stairs or slopes" as the activities where power would be injected by power unit 201, it is clear to one experienced in the art that other activities where lifting assistance is advantageous do exist (such as "coming out of squat position"). Therefore "climbing stairs or slopes" is meant to include any activity where injecting power from power unit 201 would be of advantage to the operator.

In operation, person 187 couples to (or wears) lower extremity exoskeleton 100 by coupling to human interface device 150 (a simple belt in this case of FIG. 1) and by coupling to two leg supports 101 and 102. In some embodiments as shown in FIG. 1, leg supports 101 and 102 comprise shank holding devices 137 and 138 that couple person 187 to leg supports 101 and 102.

Figure 13:
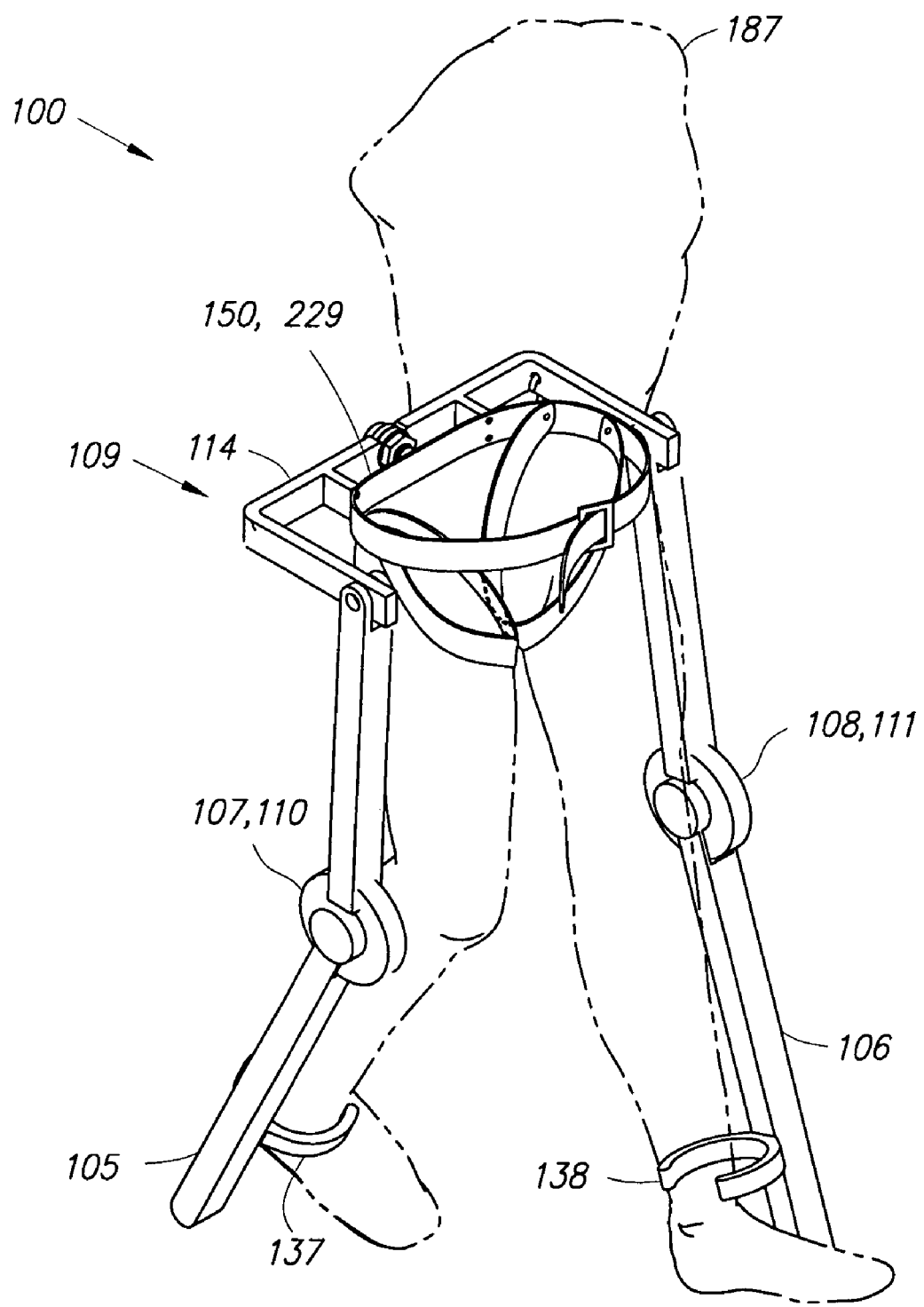
FIG. 13 is a perspective drawing in accordance with an embodiment of the invention.
Figure 28:
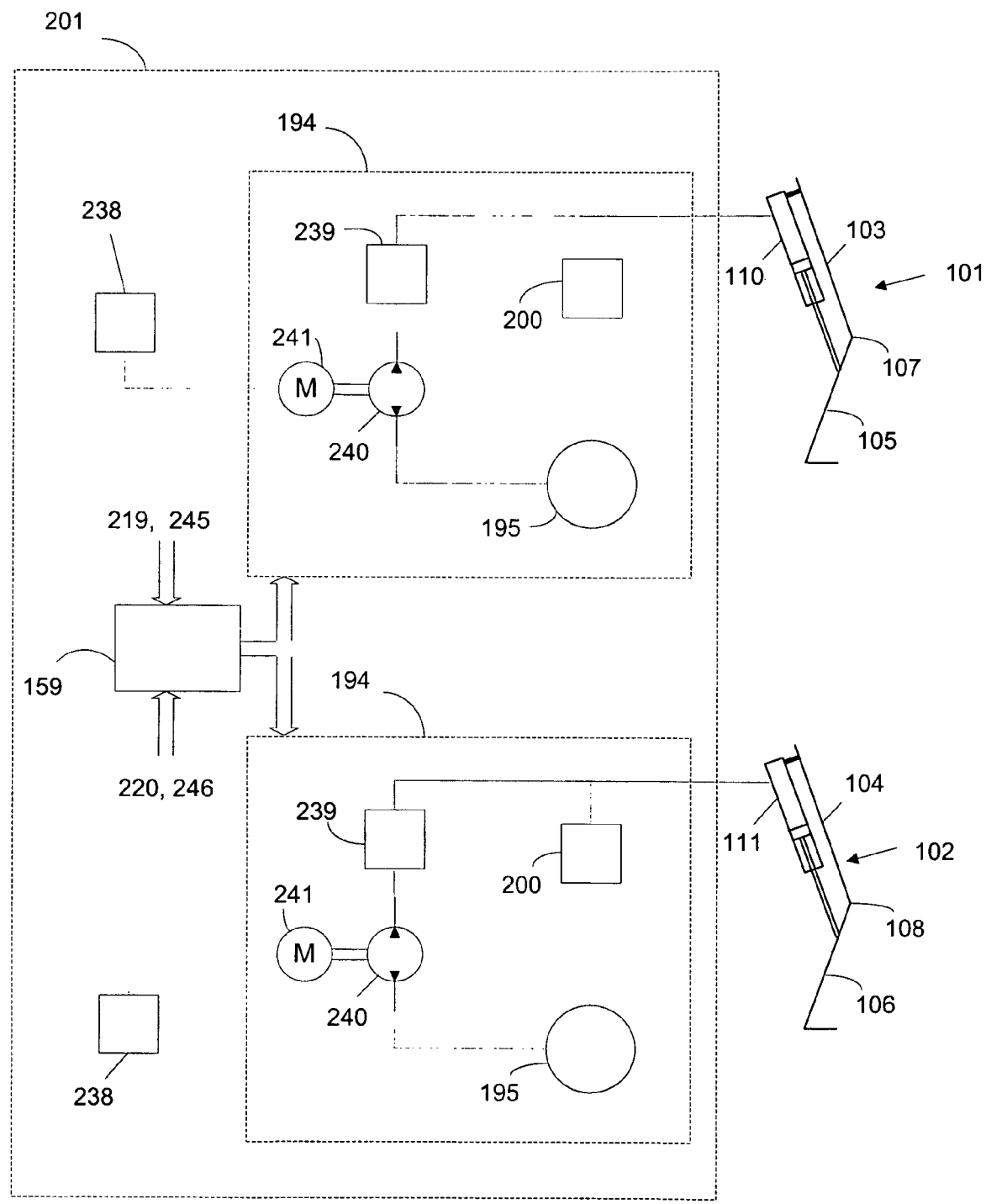
FIG. 28 is a drawing representing an embodiment of the exoskeleton power unit.

In some embodiments torque generators 110 and 111 each comprise a hydraulic torque generator. Power unit 201 is capable of providing hydraulic power for torque generators 110 and 111 and among other components, as shown in FIG. 28, includes hydraulic circuitry 194 configured to be connectable to hydraulic torque generators 110 and 111. Hydraulic circuitry 194 in power unit 201 modulates the hydraulic fluid flow to hydraulic torque generators 110 and 111. Hydraulic torque generators 110 and 111 comprise of any hydraulic torque generator or combination of torque generators capable of converting pressurized hydraulic fluid into force or torque. Examples of hydraulic torque generators 110 and 111 include, without limitation, linear hydraulic piston-cylinders, rotary hydraulic actuators, rack-and-pinion-type rotary actuators and rotary hydraulic vane type actuators where pressurized hydraulic fluid, by pushing against moving surfaces, generate force or torque. An illustration of an exoskeleton utilizing rotary hydraulic systems is shown in FIG. 13. One skilled in the art will note, however, that it is possible to construct an exoskeleton with the functionality of this invention, where torque generators 110 and 111 and the power unit 201 are a combination of electrical devices possibly including a clutch. For example, the torque generator could be a ball screw and the power unit could be a combination of a clutch (to minimize the resistance to flexion and extension during swing) and an electric motor (to inject energy).

Figure 29:
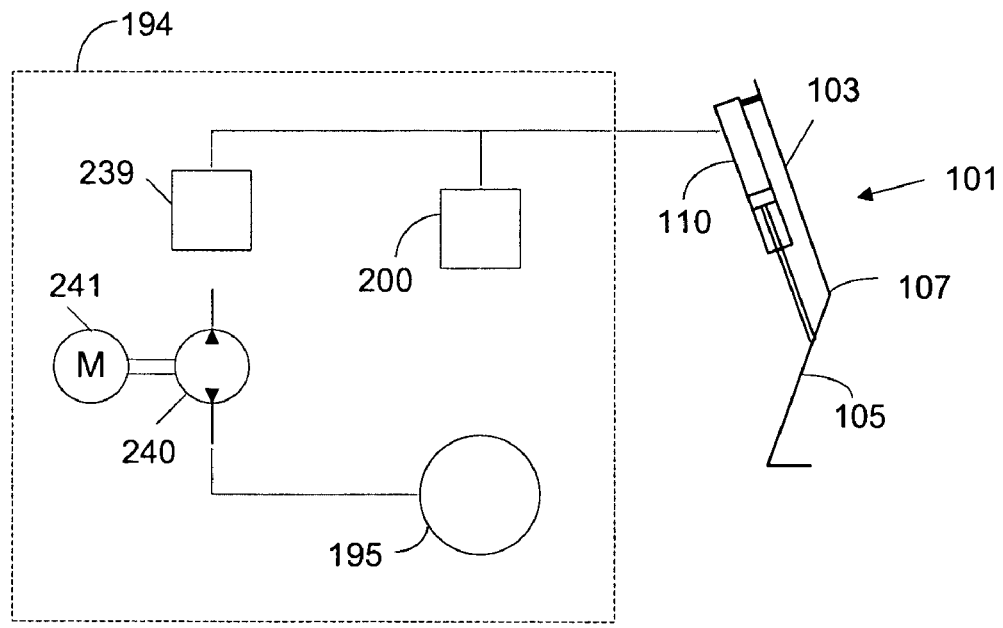
FIG. 29 is a drawing representing an embodiment of the exoskeleton hydraulic circuitry.

FIG. 29 shows an embodiment of the hydraulic circuitry 194. Hydraulic circuitry 194 comprises a hydraulic pump 240. In operation when power unit 201 operates in its first mode with respect to torque generator 110, motor 241 turns hydraulic pump 240 and hydraulic pump 240 injects hydraulic fluid into torque generator 110 causing knee joint of leg support 101 to extend. Power unit 201 further comprises power storage component 238 (as shown in FIG. 28) such as batteries and capacitors to provide power for motor 241 and other components such as sensors and electronic components. Hydraulic circuitry 194 further comprises a pump isolating valve 239. In operation, when power unit 201 operates in its first mode with respect to torque generator 110, pump isolating valve 239 connects hydraulic pump 240 to torque generator 110. Hydraulic circuitry 194 further comprises an actuated flow restricting valve 200.

In some embodiments, when leg support 101 is in a stance phase and is bent or positioned to climb stairs or a slope, power unit 201 operates in its first mode with respect to torque generator 110. In this first mode, actuated flow restricting valve 200 is shut and pump isolating valve 239 is open. This allows hydraulic pump 240 to inject hydraulic fluid to hydraulic torque generator 110 from a source of hydraulic fluid (e.g. hydraulic reservoir 195 in FIG. 29) causing knee joint 107 to extend.

In some embodiments, when leg support 101 is in a stance phase, but is not bent or positioned to climb stairs or a slope, power unit 201 operates in its second mode with respect to torque generator 110. In this second mode, pump isolating valve 239 disconnects the fluid flow between hydraulic pump 240 and torque generator 110 and actuated flow restricting valve 200 restricts the fluid flow from torque generator 110. This causes knee joint 107 to resist flexion.

In some embodiments, when leg support 101 is in a swing phase, power unit 201 operates in its third mode. In this third mode, actuated flow restricting valve 200 is open and allows for the minimum resistance hydraulic fluid flow between hydraulic torque generator 110 and a source of fluid (e.g., hydraulic reservoir 195). This allows leg support 101 to be moved with little or no resistance.

In FIGS. 29 through 35, hydraulic reservoir 195 is used to represent the source of fluid. One can use a double-acting hydraulic cylinder with rods on both ends of the piston instead of a single-acting hydraulic cylinder eliminating hydraulic reservoir 195. Although it is shown by hydraulic reservoir 195, source of fluid refers to either a hydraulic reservoir or the other chamber in a double acting hydraulic cylinder with rods on both ends.

Actuated flow restricting valve 200 comprises any valve or combination of valves capable of performing the indicated functions. Examples of actuated flow restricting valve 200 include, without limitation, flow control valve, pressure control valve, actuated needle valves, solenoid valves and on-off valve. Motor 241 comprises any device or combination of devices capable of driving hydraulic pump 240. Examples of motor 241 include, without limitation, electric motors, including, without limitation, AC (alternating current) motors, brush-type DC (direct current) motors, brushless DC motors, electronically commutated motors (ECMs), stepping motors, and combinations thereof. In some embodiments motor 241 is an internal combustion device where a fuel is combusted to create motion. Although we state that electric motor 241 turns hydraulic pump 240, one skilled in the art can realize that both motor 241 and hydraulic pump 240 may have other type of non-rotational couplings such as reciprocating linear motion.

Figure 30:
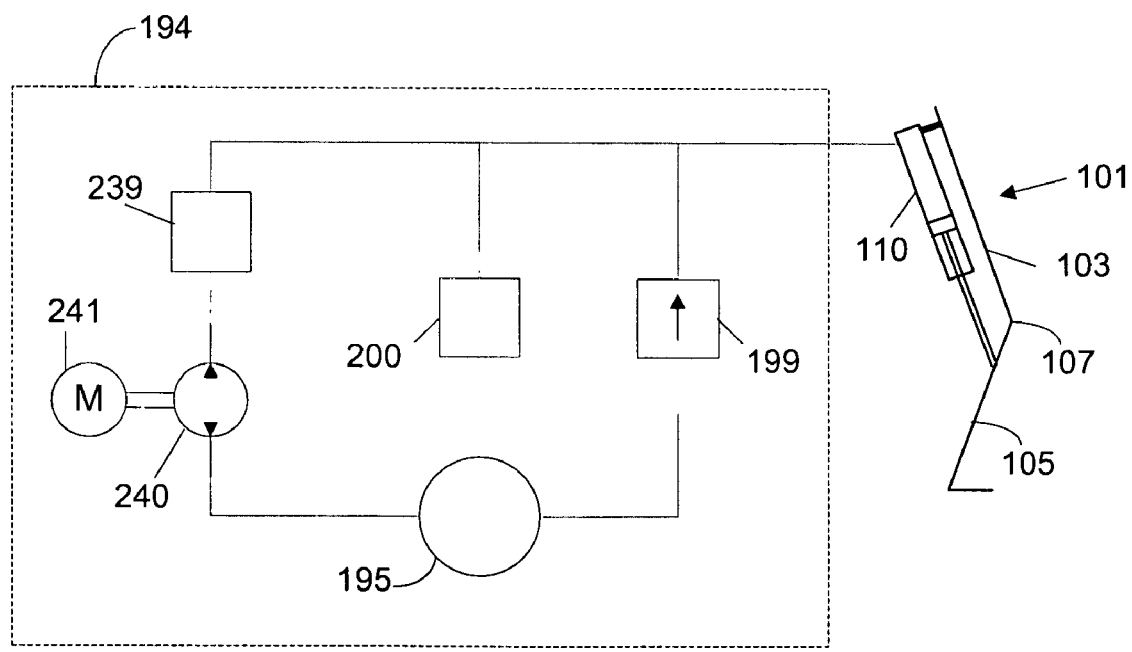
FIG. 30 is a drawing representing an embodiment of the exoskeleton hydraulic circuitry.

FIG. 30 represents another embodiment of the hydraulic circuitry 194. This embodiment is similar to embodiment of FIG. 29 but a hydraulic check valve (one way valve) 199 has been added that connects a source of hydraulic fluid (e.g., hydraulic reservoir 195) to torque generator 110. This allows free extension of the knee joint of leg support 101 when power unit 201 operates in all three modes.

Figure 31:
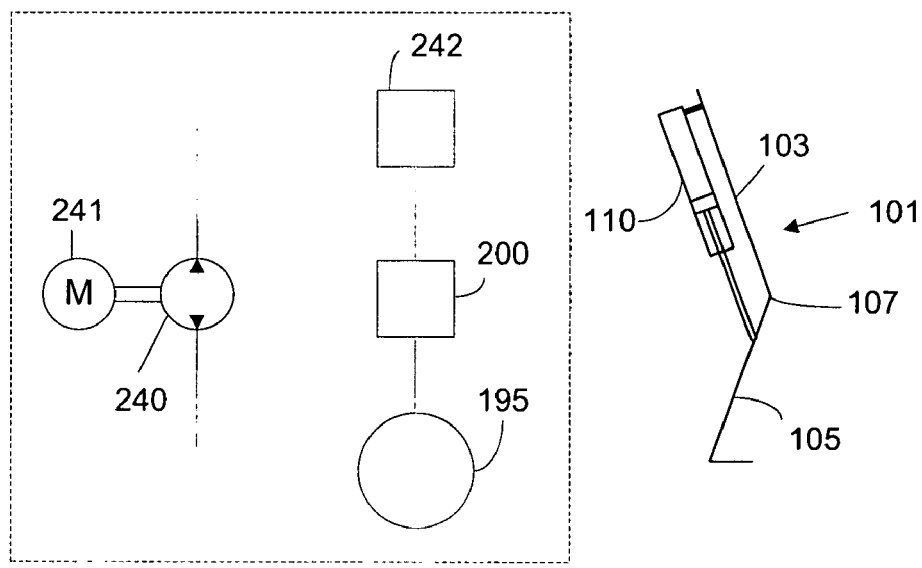
FIG. 31 is a drawing representing an embodiment of the exoskeleton hydraulic circuitry.

FIG. 31 represents another embodiment of the hydraulic circuitry 194 where a pump three-way valve 242 connects hydraulic torque generator 110 to a hydraulic reservoir 195 either through an actuated flow restricting valve 200 or through a hydraulic pump 240. When power unit 201 is operating in its first mode with respect to torque generator 110, pump three-way valve 242 connects hydraulic torque generator 110 to hydraulic pump 240 otherwise pump three-way valve 242 connects hydraulic torque generator 110 to actuated flow restricting valve 200. For example when leg support 101 is either bent or posed to climb stairs or a slope and is in stance phase, power unit operates in its first mode. In this first mode, pump three-way valve 242 connects hydraulic torque generator 110 to hydraulic reservoir 195 through hydraulic pump 240. This allows hydraulic pump 240 to inject fluid to hydraulic torque generator 110 from hydraulic reservoir 195 causing knee joint 107 to extend. When leg support 101 is not postured to climb stairs or a slope, but is in a stance phase, power unit 201 operates in its second mode. In this second mode, pump three-way valve 242 connects hydraulic torque generator 110 to hydraulic reservoir 195 through actuated flow restricting valve 200. Actuated flow restricting valve 200 restricts the hydraulic fluid flow from torque generator 110 causing knee joint 107 to resist flexion. When leg support 101 is in a swing phase, power unit 201 operates in its third mode. In this third mode, pump three-way valve 242 connects hydraulic torque generator 110 to hydraulic reservoir 195 through actuated flow restricting valve 200 and actuated flow restricting valve 200 opens and allows for the minimum resistance hydraulic fluid flow between hydraulic torque generator 110 and hydraulic reservoir 195. This allows leg support 101 to be moved with little or no resistance.

Figure 32:
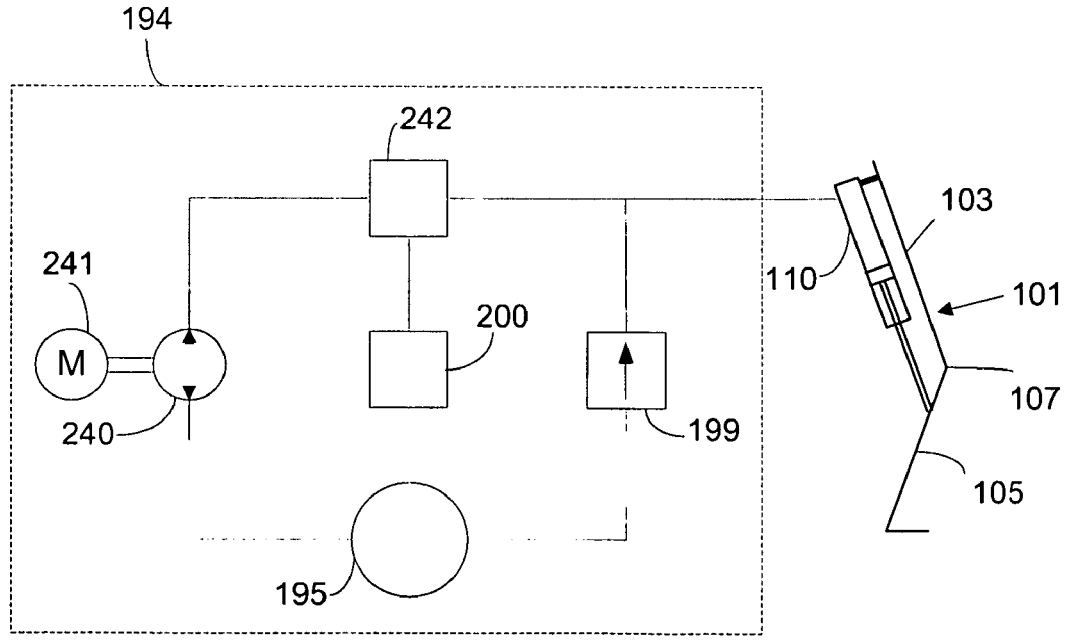
FIG. 32 is a drawing representing an embodiment of the exoskeleton hydraulic circuitry.

FIG. 32 represents another embodiment of the hydraulic circuitry 194. This embodiment is similar to embodiment of FIG. 31 but a check valve 199 has been added to allow for minimum resistance to extension of the knee joint of leg support 101 at all times.

Figure 33:
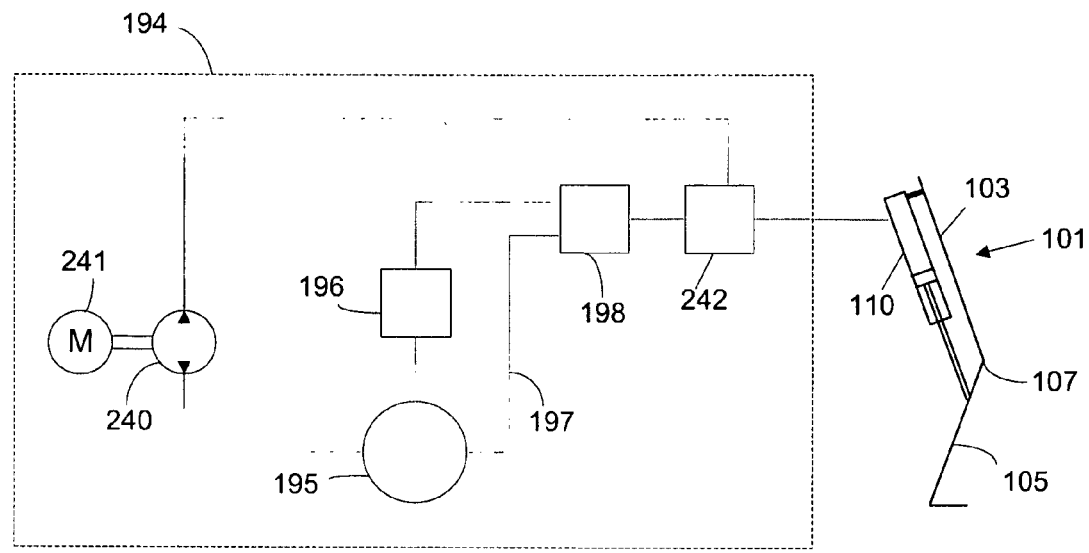
FIG. 33 is a drawing representing an embodiment of the exoskeleton hydraulic circuitry.

FIG. 33 represents another embodiment of the hydraulic circuitry 194 where actuated flow restricting valve 200 has been removed. An additional hydraulic three-way valve 198 has been added which selects between a non-actuated flow restricting valve 196 and a bypass line 197. The non-actuated flow restricting valve 196 can be a much simpler device and can either be a simple orifice or an adjustable device such as a needle valve. In operation, when leg support 101 is in a stance phase and is either bent or positioned to climb stairs or a slope, power unit 201 operates in its first mode. In this first mode, pump three-way valve 242 connects hydraulic torque generator 110 to hydraulic reservoir 195 through hydraulic pump 240. This allows hydraulic pump 240 to inject fluid to hydraulic torque generator 110 from hydraulic reservoir 195 causing knee joint 107 to extend. When leg support 101 is in its stance phase, but is neither bent nor positioned to climb stairs or a slope, power unit 201 operates in its second mode. In this second mode, pump three-way valve 242 connects hydraulic torque generator 110 to hydraulic three-way valve 198. Hydraulic three-way valve 198 connects pump three-way valve 242 to hydraulic reservoir 195 through non-actuated flow restricting valve 196 thereby reducing flow and increasing the impedance of hydraulic torque generator 110. This causes knee joint 107 to resist flexion. When leg support 101 is in swing phase, power unit 201 operates in its third mode. In this third mode, pump three-way valve 242 connects hydraulic torque generator 110 to hydraulic three-way valve 198. Hydraulic three-way valve 198 connects pump three-way valve 242 to hydraulic reservoir 195 through bypass line 197 thereby increasing fluid flow and decreasing the impedance of hydraulic torque generator 110. This allows leg support 101 to be moved with little or no resistance.

Figure 34:
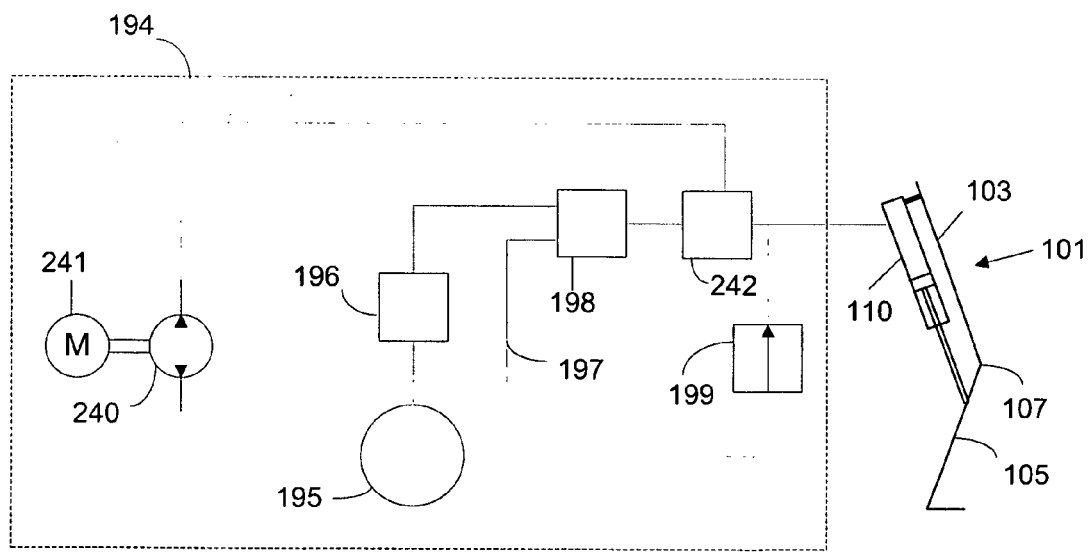
FIG. 34 is a drawing representing an embodiment of the exoskeleton hydraulic circuitry.

FIG. 34 represents another embodiment of the hydraulic circuitry 194. This embodiment is similar to embodiment of FIG. 33 but a check valve 199 has been added to allow for minimum resistance to extension of the knee at all times.

It is important to note that there is a plethora of possible hydraulic circuits which could be used to create the behavior which is the subject of this invention. Inspection of various embodiments of the hydraulic circuitry 194, reveals that each torque generator is coupled to a power injecting subcomponent of power unit 201, capable of injecting power to a torque generator, and a power dissipating subcomponent of power unit 201 capable of dissipating power from the torque generator. For example, examination of FIG. 29 shows that actuated flow restricting valve 200 is power dissipating subcomponent while hydraulic pump 240 is a power injecting subcomponent. Power unit 201 selects which subcomponent torque generator will be connected to.

In some embodiments, as shown in FIG. 28, power unit 201 further comprises a signal processor 159 capable of creating command signals for various components of power unit 201 to control power unit 201. Signal processor comprises an element or combination of elements selected from a group consisting of analog devices; analog computation modules; digital devices including, without limitation, small-, medium-, and large-scale integrated circuits, application specific integrated circuits, programmable gate arrays, and programmable logic arrays; and digital computation modules including, without limitation, microcomputers, microprocessors, microcontrollers, and programmable logic controllers. In some embodiments signal processor 159 comprises an element or combination of elements selected from a group consisting of electromechanical relays or MOSFET switches. Signal processor 159 generates command signals for said hydraulic circuitry from stance signals 219 and 220, and angle signals 245 and 246 or combination thereof.

It is also important to note that any of these hydraulic circuits could be used to capture energy when walking down a slope or stairs. Considering FIG. 29, one can see that if the power unit detected that the operator were walking down a steep slope and the leg was in stance phase, the pump isolating valve 239 could be opened and actuated flow restricting valve 200 could be closed. This would divert fluid under pressure backwards into the hydraulic pump 240 which could then behave as a hydraulic motor (if properly configured) turning electric motor 241 backwards and generating electricity. If the energy storage medium in power unit 201 was capable of accepting such energy, like a battery, then this energy could be captured and used later to provide assistance during climbing a slope or stairs. (Note that power unit 201 can detect the condition of walking down a slope by observing a knee angle near 180 at the beginning of stance and a much lower angle at the end of stance). The system could behave as before during swing (providing minimum resistance to flexion or extension), during stance while climbing (injecting power), and during stance while walking on near level ground (dissipating energy through a device such as a flow restricting valve.)

Figure 35:
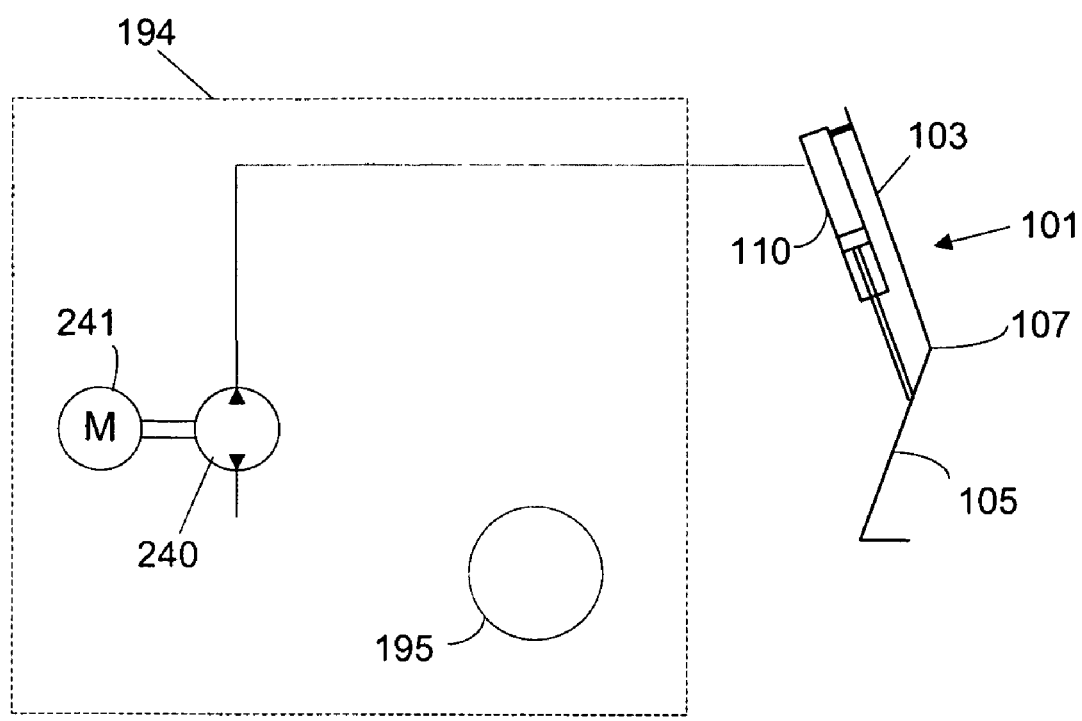
FIG. 35 is a drawing representing an embodiment of the exoskeleton hydraulic circuitry.

In fact, if hydraulic pump 240 and motor 241 could be designed to provide the correct amount of resistance to flexion during stance and minimal resistance during swing while walking on level ground, the actuated flow restricting valve 200 could be eliminated, and the simple system shown in FIG. 35 could be used. However, this would only be economical from a power consumption viewpoint, if the motor 241 would consume only negligible amounts of power or none at all while the leg was in stance while walking on level or near-level ground.

One skilled in the art will note that in all of these circuits, hydraulic reservoir 195 from one leg could be combined with the hydraulic reservoir from the other leg. Also, the separate motors 241, hydraulic pump 240, and reservoirs 195 could be combined in the form of a more tradition hydraulic power supply consisting of a low pressure reservoir, a single motor and hydraulic pump, a high pressure reservoir, and some control valves which let the correct flow of hydraulic fluid out of the high pressure reservoir and into each of the hydraulic torque generators. This design, however, is not as advantageous as a single motor per hydraulic torque generator, because of the large amount of power wasted by such control valves.

It should also be noted that all pressure relief valves have been omitted from the hydraulic diagrams for clarity.

Further discussing the geometry of the exoskeleton shown in FIG. 1, in some embodiments as shown in FIG. 1, exoskeleton trunk 109 includes two hip links 114 and 115 rotatably connectable to thigh links 103 and 104 at hip flexion-extension joints 125 and 126, allowing for the flexion and extension of leg supports 101 and 102 about hip flexion-extension axes 151 and 152 respectively. In some embodiments, hip links 114 and 115 are rotatably connected to each other at abduction-adduction joint 113 allowing for abduction and/or adduction of leg supports 101 and 102. Abduction and adduction of leg supports 101 and 102 are shown by arrows 217 and 218 respectively.

In some embodiments, the energy required for flexion and extension movement between leg supports 101 and 102 and exoskeleton trunk 109 over a cyclic hip motion is provided by said person. In some other embodiments, one can couple torque generators to hip joints 125 and 126.

In some embodiments, exoskeleton trunk 109 is configured to hold a rear load 118 behind person 187. In some embodiments, as shown in FIG. 1, rear load 118 is held by hip links 114 and 115. In some embodiments, exoskeleton trunk 109 further comprises extension frames 119 and 120 configured to hold a front load 154 in front of person 187. In some embodiments (as shown in FIG. 1) extension frames 119 and 120 are connectable to hip links 114 and 115. Examples of rear load 118 and front load 154 include without limitation, backpack, baby carrier, food containers, sacks, water jugs, tool boxes, barrels, ammunition, weaponry, bedding, first aid supplies, golf bags, mail bags, camera, leaf blower, compressor, electromechanical machineries and combinations thereof. In some embodiments, rear load 118 and/or front load 154 are another person being carried by person 187. In some embodiments, exoskeleton trunk 109 supports a portion of the weight of person 187 through human interface device 150.

Figure 3:
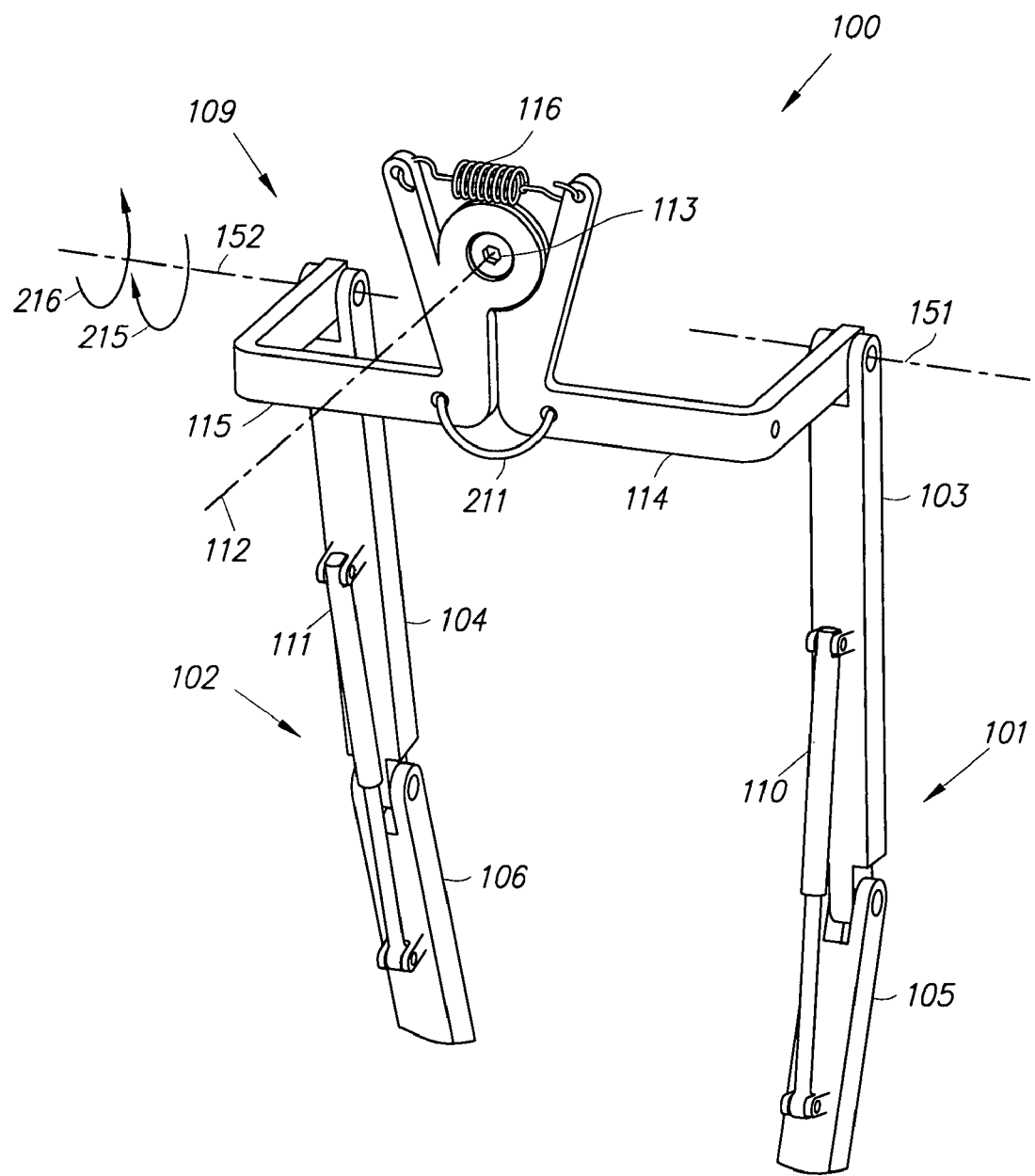
FIG. 3 is a perspective drawing in accordance with an embodiment of the present invention.

FIG. 3 shows another embodiment of the invention where exoskeleton trunk 109 further comprises a hip resilient element 116 configured to apply a torque between hip links 114 and 115. Examples of a hip resilient element include, without limitation, extension spring, compression spring, leaf spring, gas spring, air spring, rubber, elastomer, surgical tube, bungee cord and combinations thereof. The stiffness of hip resilient element 116 may be chosen such that its force generally holds up the weight of the leg supports 101 or 102 during swing phase.

Some embodiments, as shown in FIG. 3, may also include a hip abduction stop 211 which limits or prevents hip links 114 and 115 from abducting with respect to each other. In the particular embodiment shown in FIG. 3, abduction stop 211 is created using a wire rope. Wire rope 211 prevents abduction of leg supports 101 and 102 from occurring but allows adduction of leg supports 101 and 102.

Figure 4:
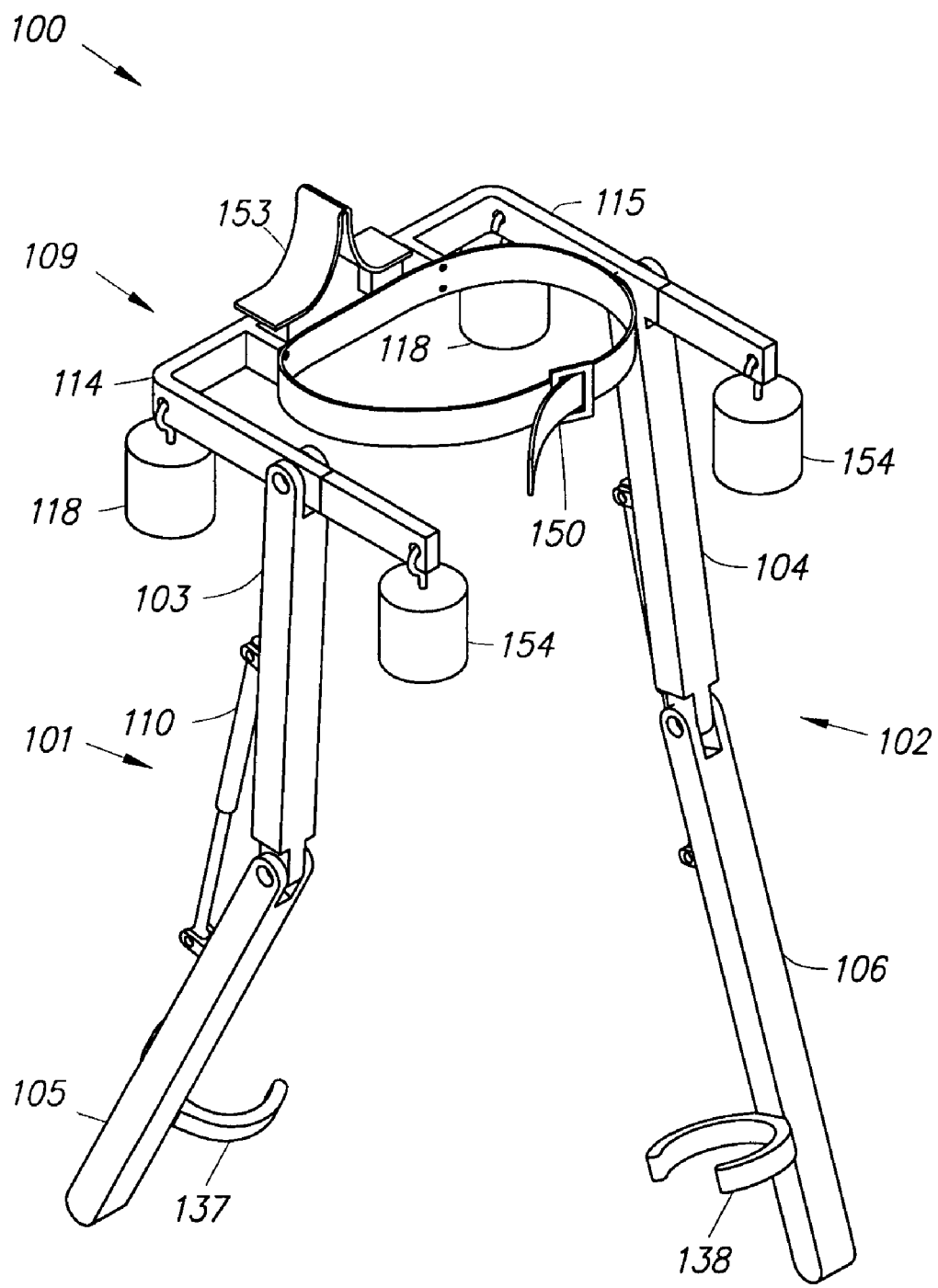
FIG. 4 is a perspective drawing in accordance with an embodiment of the present invention.

In accordance with another embodiment of the invention, FIG. 4 is a perspective drawing where exoskeleton trunk 109 includes two hip links 114 and 115 rotatably connectable to thigh links 103 and 104 allowing for flexion and extension of support legs 101 and 102 relative to exoskeleton trunk 109, wherein hip links 114 and 115 are compliantly connected to each other allowing for abduction and/or adduction of leg supports 101 and 102. In the example shown in FIG. 4, this is accomplished by leaf spring 153.

Figure 5:
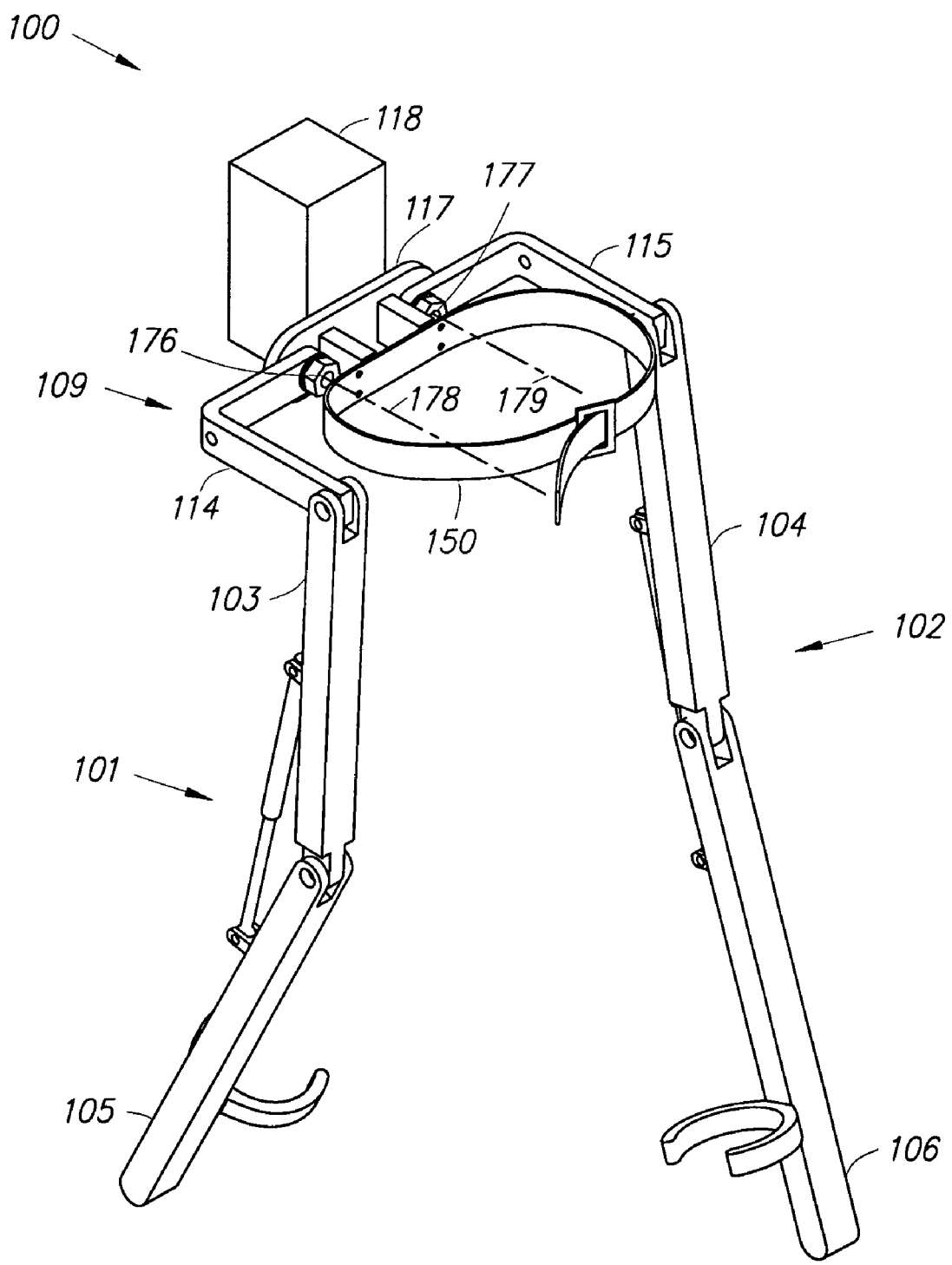
FIG. 5 is a perspective drawing in accordance with an embodiment of the present invention.

In accordance with another embodiment of the invention, FIG. 5 is a perspective drawing wherein exoskeleton trunk 109 further comprises a connecting bracket 117 configured to transfer the weight of rear load 118 to exoskeleton trunk 109. Exoskeleton trunk 109 further comprises two hip links 114 and 115 rotatably connectable to thigh links 103 and 104 allowing for flexion and extension of leg supports 101 and 102 relative to exoskeleton trunk 109. Hip links 114 and 115 are rotatably connected to connecting bracket 117 via two hip abduction-adduction joints 176 and 177 and rotate about two hip abduction-adduction axes 178 and 179. In some embodiments, hip abduction-adduction axes 178 and 179 are generally parallel to each other. In some embodiments, hip abduction-adduction joints 176 and 177 coincide with each other. Furthermore, in some embodiments, as shown in FIG. 6, hip abduction-adduction joints 176 and 177 coincide with each other forming hip abduction-adduction joint 113 and hip abduction-adduction axes 178 and 179 become one hip abduction-adduction axis 112.

Figure 6:
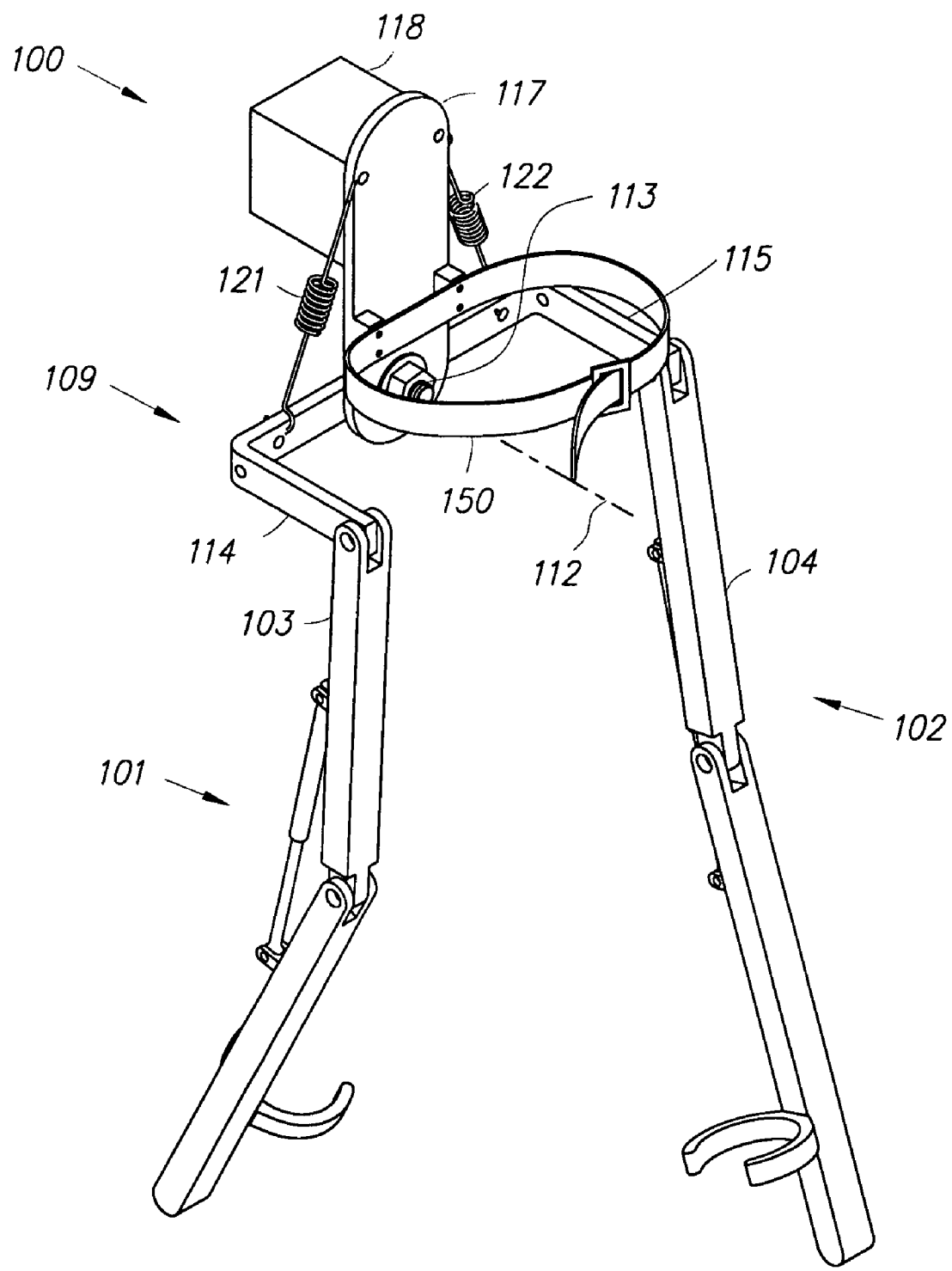
FIG. 6 is a perspective drawing in accordance with an embodiment of the present invention.
Figure 7:
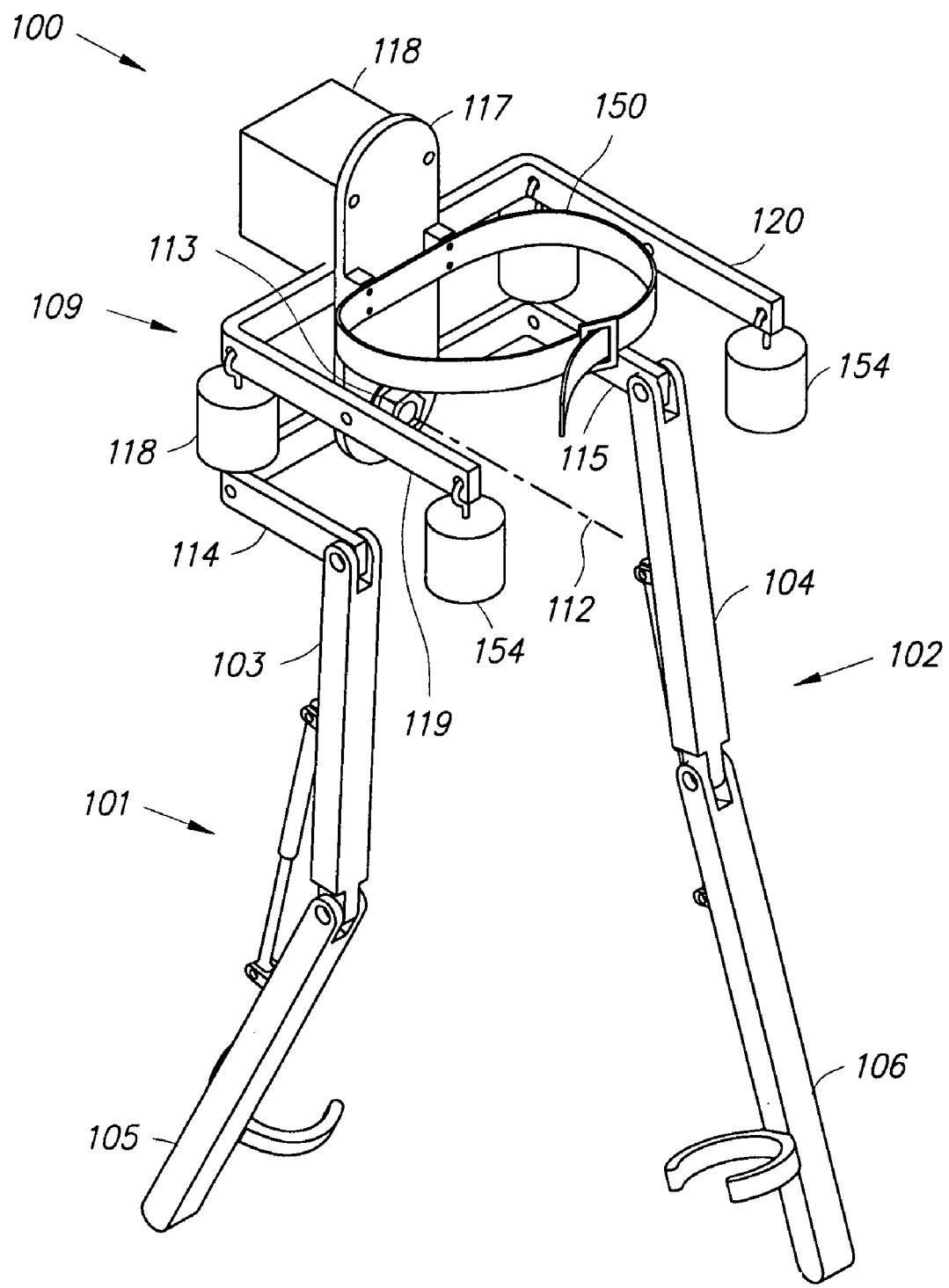
FIG. 7 is a perspective drawing in accordance with an embodiment of the present invention.

In some embodiments, as shown in FIG. 6, exoskeleton trunk 109 further comprises hip abduction-adduction resilient elements 121 and 122 configured to apply torques between hip links 114 and 115 and connecting bracket 117. Examples of hip abduction-adduction resilient elements include, without limitation, extension spring, compression spring, gas spring, air spring, rubber, surgical tube, leaf springs, bungee cord and combinations thereof. The stiffness of hip abduction-adduction resilient elements 121 and 122 may be chosen such that its force generally holds up the weight of the leg supports 101 or 102 during swing phase and aid the person in keeping the load oriented vertically while walking. In some embodiments as shown in FIG. 7, connecting bracket 117 further comprises extension frames 119 and 120 configured to hold front load 154 in front of person 187.

In some embodiments, as shown in FIGS. 1, 5, 6 and 7, exoskeleton trunk 109 comprises human interface device 150 capable of coupling person 187 to lower extremity exoskeleton 100. Examples of human interface device 150 comprise an element or combination of elements including, without limitation, vests, belts, straps, shoulder straps, chest straps, body cast, harness, and waist belts. In some embodiment human interface device 150 transfers a portion of the weight of person 187 to exoskeleton trunk 109. FIG. 13 shows an embodiment where human interface device 150 comprises a specially-designed harness 229 to fit the body of person 187. Harness 229 transfers a portion of the weight of person 187 to exoskeleton trunk 109.

Figure 8:
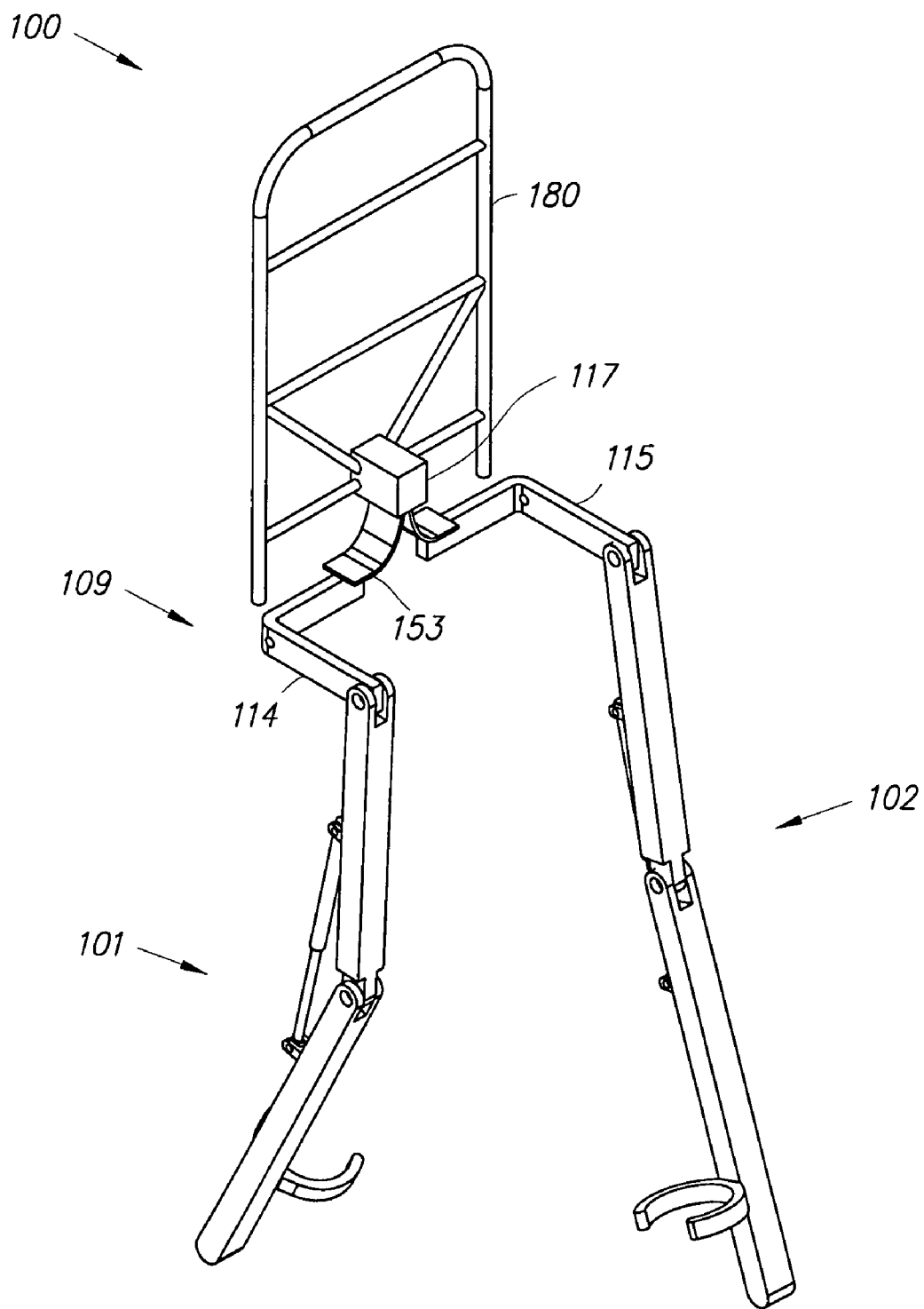
FIG. 8 is a perspective drawing in accordance with an embodiment of the present invention.

In some embodiments, as shown in FIG. 8, hip links 114 and 115 are compliantly connected to connecting bracket 117. In the embodiment shown in FIG. 8, this is accomplished by a hip resilient member 153 which in this case is a leaf spring.

In some embodiments, as shown in FIG. 8, exoskeleton trunk 109 comprises a backpack frame 180 that allows a backpack to be coupled to lower extremity exoskeleton 100. In some embodiments, backpack frame 180 is connected to connecting bracket 117. The human interface devices 150 (such as a belt and shoulder straps) have been omitted in this figure for clarity.

Figure 9:
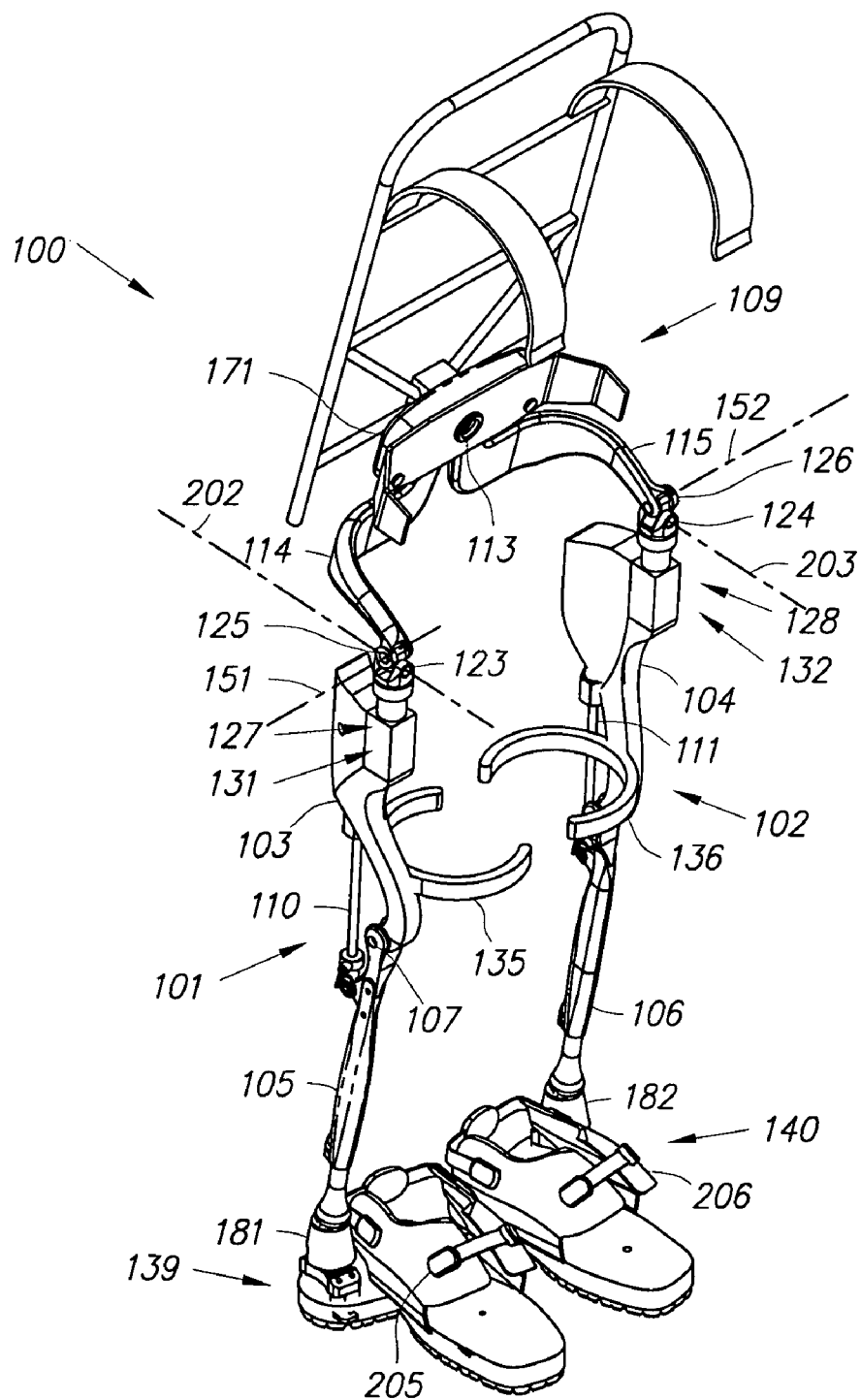
FIG. 9 is a perspective drawing in accordance with an embodiment of the present invention.

In accordance with another embodiment, FIG. 9 is a perspective drawing wherein leg supports 101 and 102 further include thigh abduction-adduction joints 123 and 124 configured to allow abduction and/or adduction of leg supports 101 and 102 about axes 202 and 203 respectively. In some embodiments, thigh abduction-adduction joints 123 and 124 are located below hip flexion-extension joints 125 and 126. These joints are shown in greater detail in FIG. 10 which is a partial view of the same embodiment of FIG. 9.

Figure 10:
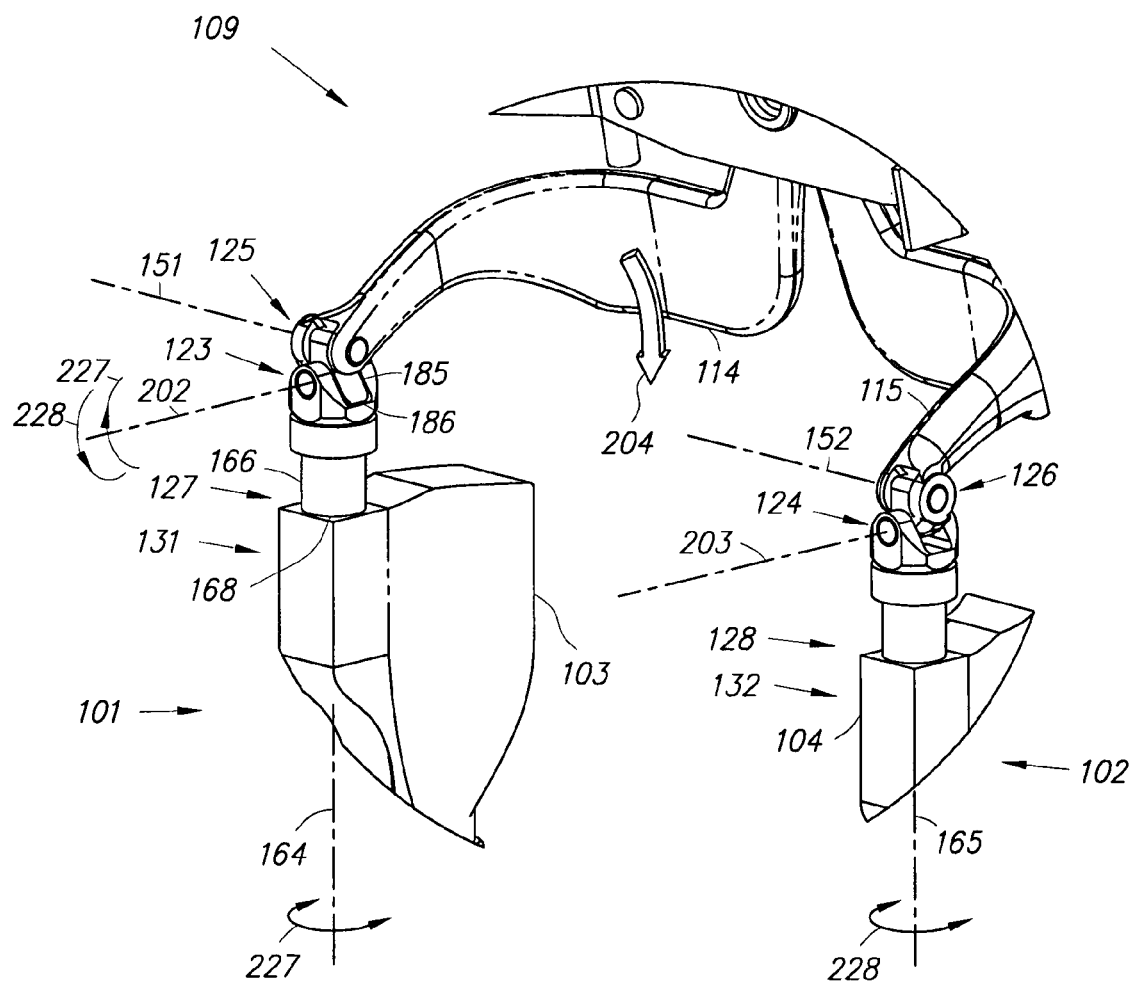
FIG. 10 is a partial view of the invention of the embodiment of FIG. 9.

In some embodiments, as shown in FIG. 10, leg supports 101 and 102 comprise a thigh adduction stop 185 which limits or prevents thigh links 103 and 104 from adducting at joint 123 and 124. Abduction and adduction of leg support 101 are shown by arrows 227 and 228 respectively. In the particular embodiment shown in FIG. 10, thigh abduction-adduction joint 123 includes a thigh adduction stop 185 which bears on a thigh stop surface 186. Thigh adduction stop 185 limits the adduction of thigh abduction-adduction joint 123. The unrestricted adduction of thigh abduction-adduction joint 123, during stance phase, would cause hip link 114 to move downwardly along arrow 204 during stance thereby dropping (lowering) the load. Such abduction-only joints for joints 123 and 124 are useful in allowing the person to squat naturally. In some embodiments like the one shown in FIGS. 9 and 10, such abduction joints are generally located below hip flexion-extension joints 125 and 126.

Figure 11:
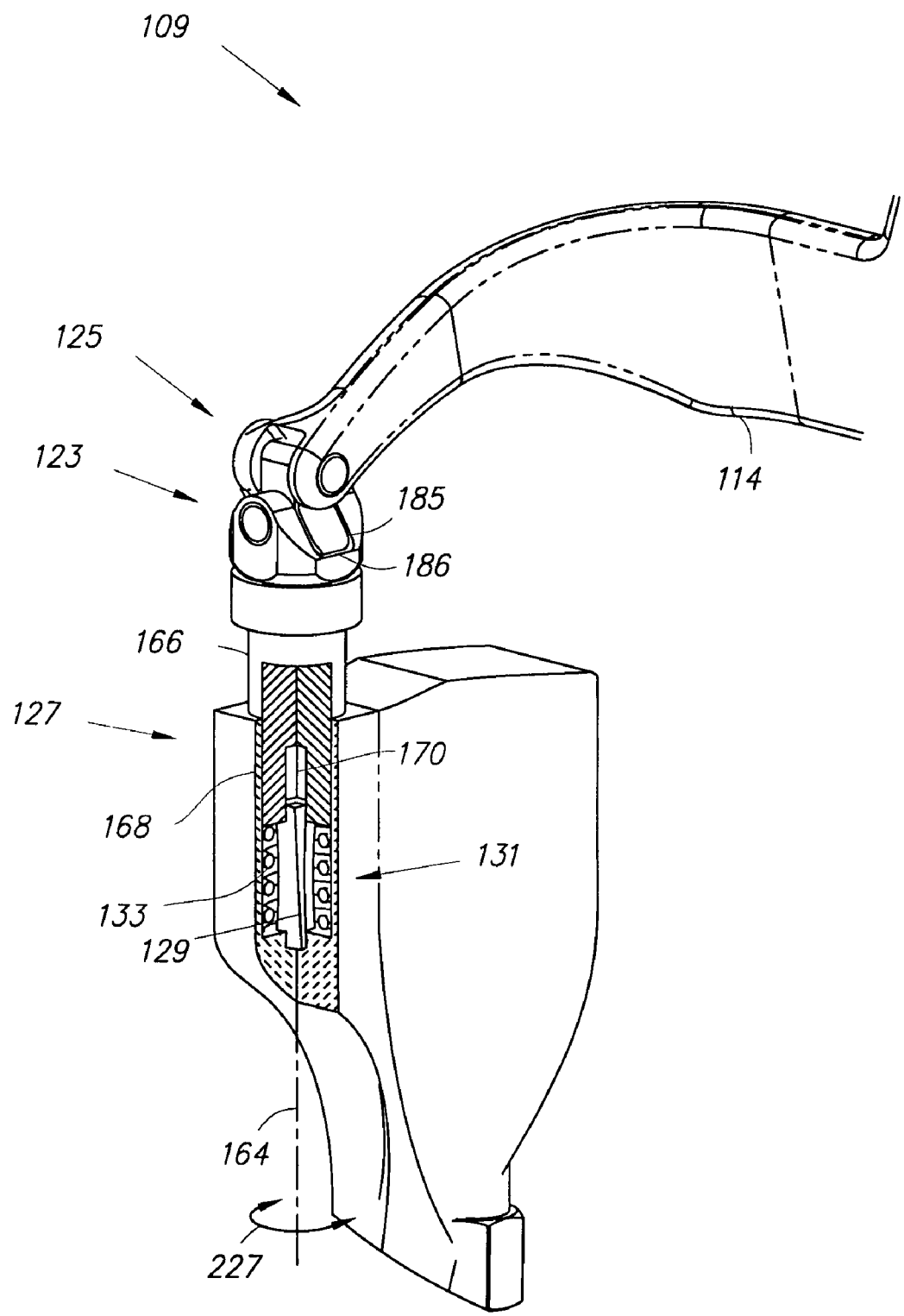
FIG. 11 is a partial view of the invention of the embodiment of FIG. 9.

In some embodiments, as shown in FIGS. 9 and 10, leg supports 101 and 102 further include thigh rotation joints 127 and 128 configured to allow rotation of leg supports 101 and 102. Rotation joints 127 and 128 are generally located above knee joints 107 and 108. Lines 164 and 165 represent the rotation axes of rotation joints 127 and 128. In FIGS. 10 and 11, this is accomplished by providing for a sliding contact between the hip rotation shaft 166 and the hip rotation journal 168. The parts included in the joint which prevent it from pulling apart have been omitted for simplicity, but one skilled in the art will note that there are many ways of retaining such shafts in such journals.

In some embodiments, as shown in FIG. 11, rotation joints 127 and 128 further comprise a rotation resilient element 129. This rotation resilient element acts as a torsion spring and provides a restoring torque which generally restores the leg support back to the neutral position shown in FIG. 9. Rotation resilient element 129 can be constructed in many ways with the particular cross section shown in FIG. 11 being advantageous when using an elastomeric material to construct the element. Rotation resilient element 129 is shown partially deflected for illustration purposes.

Also, in some embodiments, as shown in FIG. 10 and FIG. 11, leg supports 101 and 102 further comprise compression-elongation mechanisms 131 and 132 configured to change the distance between exoskeleton trunk 109 and the respective knee flexion-extension joints 107 and 108. In some embodiments, compression-elongation mechanisms 131 and 132 allow for changes in the distance between the hip flexion-extension joints 125 and 126 and the respective knee flexion-extension joints 107 and 108. The compression-elongation mechanisms contracts by hip rotation shaft 166 sliding further into the hip rotation journal 168 (shown for leg 101 only). The leg rotation resilient element 129 is allowed to slide into a clearance cavity 170. In some embodiments, compression-elongation mechanism 131 and 132 further comprise a leg compression-elongation resilient element 133. This leg compression-elongation resilient element acts as a spring and provides a restoring force which generally restores the leg support back to a neutral configuration. In the embodiment of FIG. 11, this is illustrated by a helical compression spring.

Figure 12:
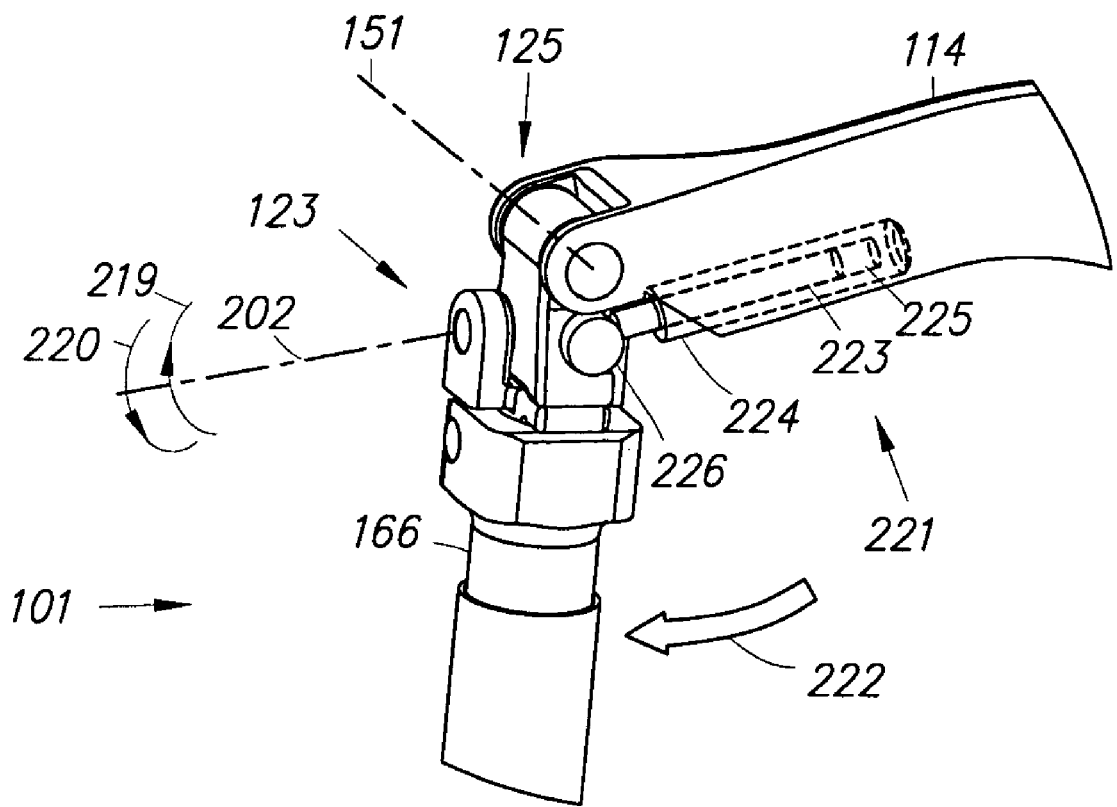
FIG. 12 is a perspective drawing in accordance with an embodiment of the present invention.

In some embodiments, as shown in FIG. 12, lower extremity exoskeleton 100 further comprises two swing resilient elements configured to apply torque between thigh links 103 and 104 and exoskeleton trunk 109. In operation swing resilient element 221 pushes leg support 101 forward along arrows 222 during swing phase. This allows the person to swing the thigh links forward with less effort. In some embodiment swing resilient element 221 is a gas spring. Gas spring 221 includes a gas spring piston 223 and a gas spring cylinder 224. In operation the force of compressed gas 225 in gas spring cylinder 224 forces gas spring piston 223 against cam 226 thereby pushing leg support 101 along arrow 222. Examples of a swing resilient element 221, include, without limitation, extension spring, compression spring, leaf spring, gas spring, air spring, rubber, elastomer, surgical tube, bungee cord and combinations thereof. The stiffness of swing resilient element 221 may be chosen to give appropriate level of comfort.

In some embodiments, as shown in FIG. 9, exoskeleton trunk cover 171 may cover some components of exoskeleton trunk 109 including parts of hip links 114 and 115. The operation of the exoskeleton trunk is the same as in FIG. 3 or 6 depending on the preferred choice of hip resilient element 116 or hip abduction-adduction resilient elements 121 and 122.

In some embodiments as shown in FIG. 9, thigh links 103 and 104 comprise thigh holding devices 135 and 136 configured to allow person 187 to couple to leg supports 101 and 102. Each thigh holding device 135 or 136 comprises an element or combination of elements including, without limitation, straps, bars, c-shape brackets, body cast, and elastomers. In some embodiments, as shown in FIG. 1, shank links 105 and 106 include comprise holding devices 137 and 138 configured to allow person 187 to couple to leg supports 101 and 102. Each shank holding device 137 and 138 comprises an element or combination of elements including, without limitation, straps, bars, c-shape brackets, body cast, and elastomers.

Figure 14:
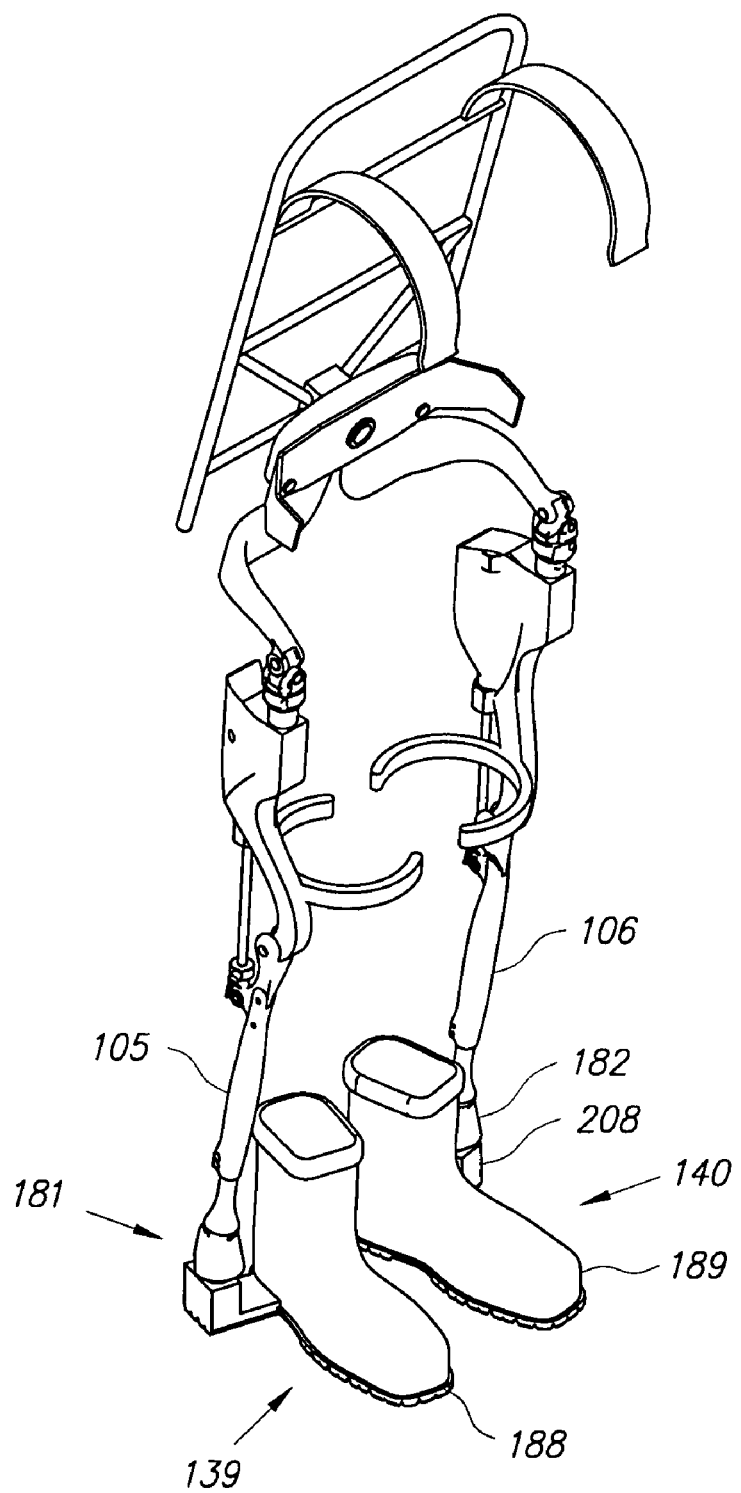
FIG. 14 is a perspective drawing in accordance with an embodiment of the exoskeleton foot.
Figure 15:
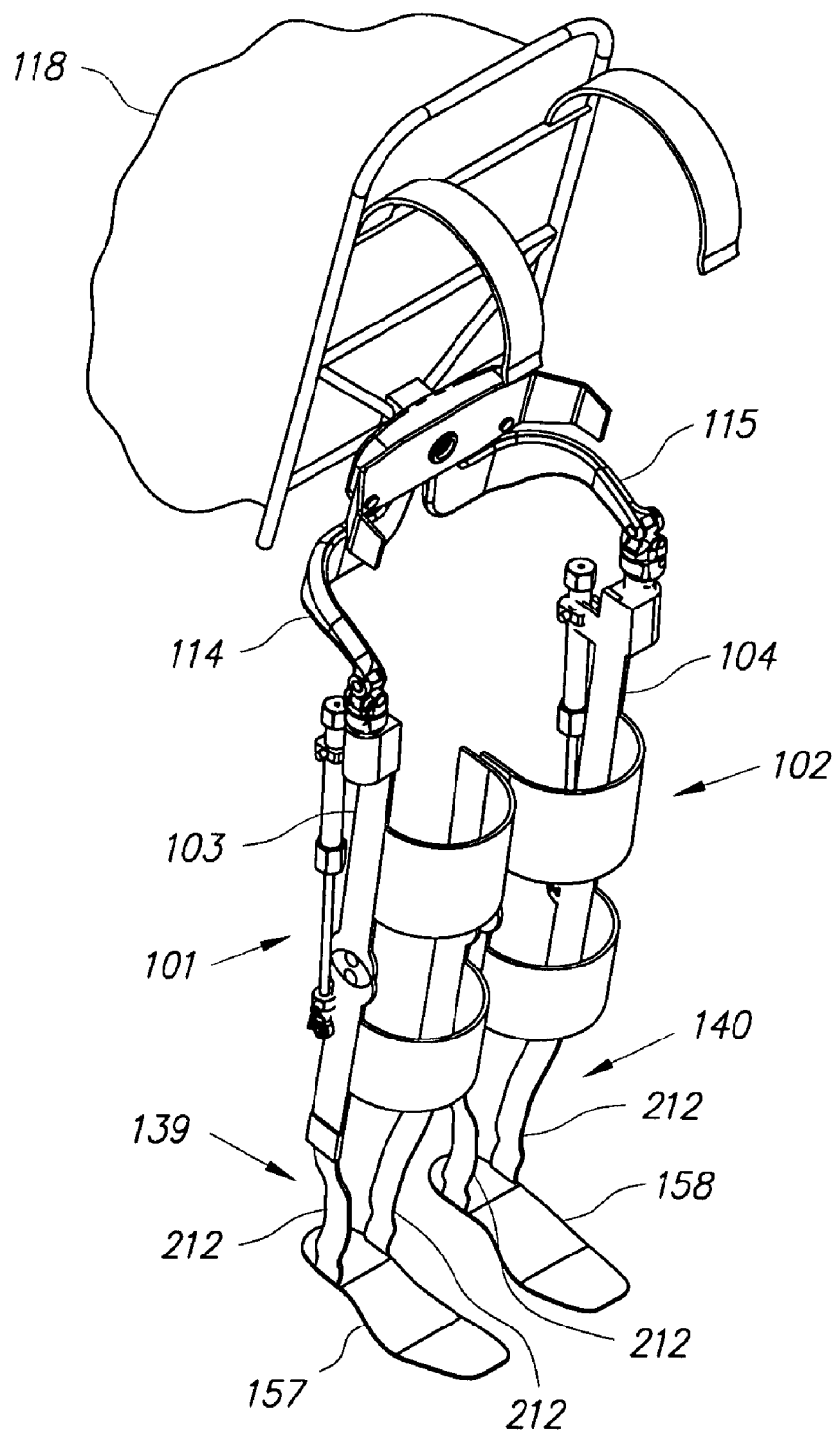
FIG. 15 is a perspective drawing in accordance with an embodiment of the exoskeleton foot.

In some embodiments, as shown in FIG. 9, leg supports 101 and 102 further comprise exoskeleton feet 139 and 140 coupled to shank links 105 and 106 respectively, allowing the transfer of forces from shank links 105 and 106 to the ground. In operation, exoskeleton feet 139 and 140 are configurable to be coupled to the feet of person 187. In some embodiments, as shown in FIG. 9, the coupling to person's feet is accomplished by using clam-shell type bindings 205 and 206 sometimes found on modern snow shoes. However, there are a great number of methods to make such a connection as can be seen on different types of snow skis, snowboards, snowshoes and other such devices. In some embodiments, as shown in FIG. 14, exoskeleton feet 139 and 140 comprise exoskeleton shoes 188 and 189 wearable by person 187 thereby allowing exoskeleton feet 139 and 140 to couple to the feet of person 187. In some embodiments, as shown in FIG. 15, exoskeleton feet 139 and 140 comprise exoskeleton insoles 157 and 158 insertable inside the person's shoes, allowing exoskeleton feet 139 and 140 to couple to the feet of person 187. Insoles 157 and 158 are flexible and therefore can bend to match the curvature of the human foot during maneuvers such as squatting. Also, the insole side supports 212 are either compliant or configured to include degrees of freedom to mimic the movement of the human ankle.

Figure 16:
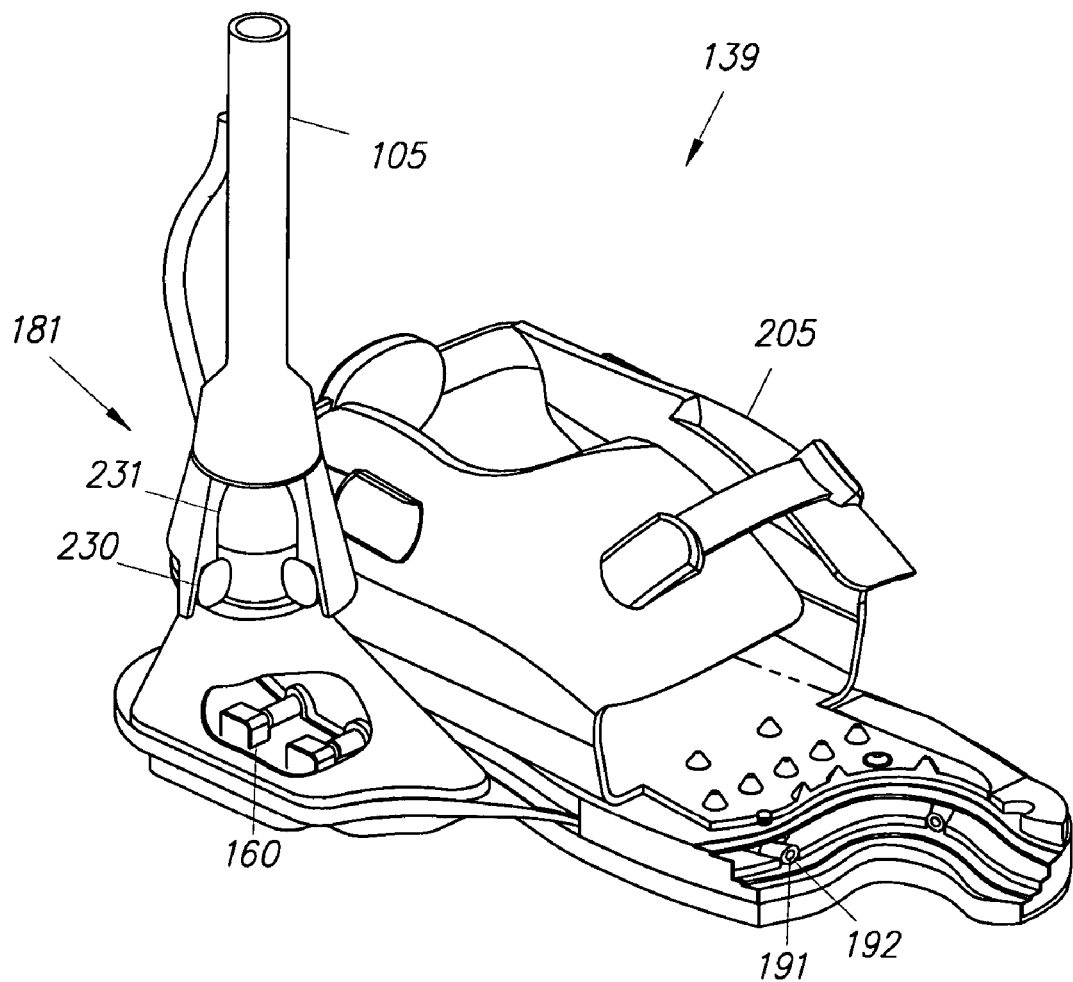
FIG. 16 is a perspective drawing in accordance with an embodiment of the exoskeleton foot.

In some embodiments, as shown in FIG. 9, exoskeleton feet 139 and 140 are compliantly coupled to shank links 105 and 106. This is accomplished using ankle resilient elements 181 and 182. FIG. 16 shows a close-up view of exoskeleton feet 139. In this example, ankle resilient elements 181 (and 182) each are constructed of a metal ball-and-socket joint 231 surrounded by an elastomer donut shape element 230 which creates compliance in all directions of rotations.

Figure 17:
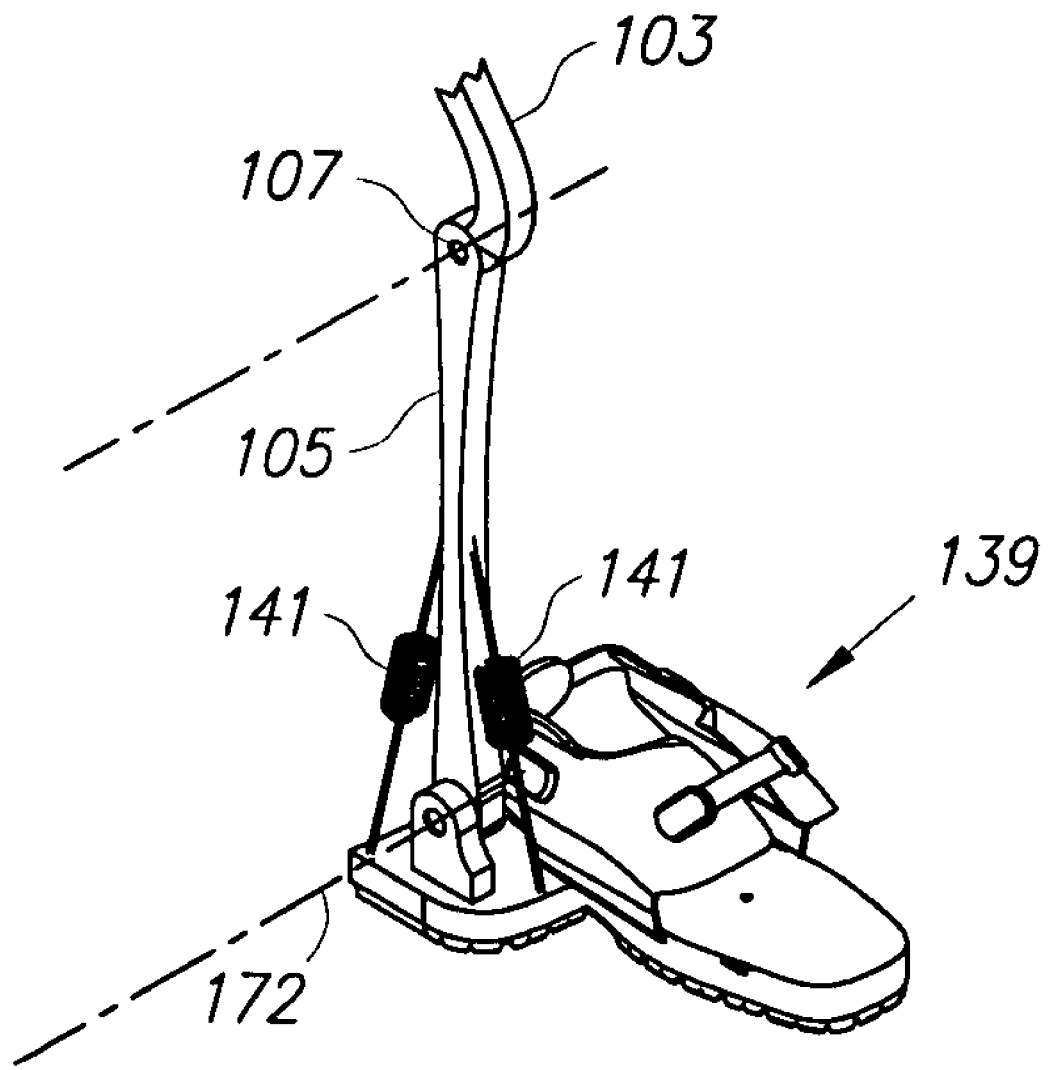
FIG. 17 is a perspective drawing in accordance with an embodiment of the exoskeleton foot.

In some embodiments, exoskeleton feet 139 and 140 rotate about two plantar-dorsi flexion axes relative to shank links 105 and 106. FIG. 17 shows an embodiment of this type of exoskeleton where ankle plantar-dorsi flexion axis 172 is generally parallel to the plantar-dorsi flexion axis in the human ankle. In some embodiments, each leg support further comprises at least one ankle plantar-dorsi flexion resilient element 141 resisting the rotation of respective exoskeleton foot about ankle plantar-dorsi flexion axis 172.

Figure 18:
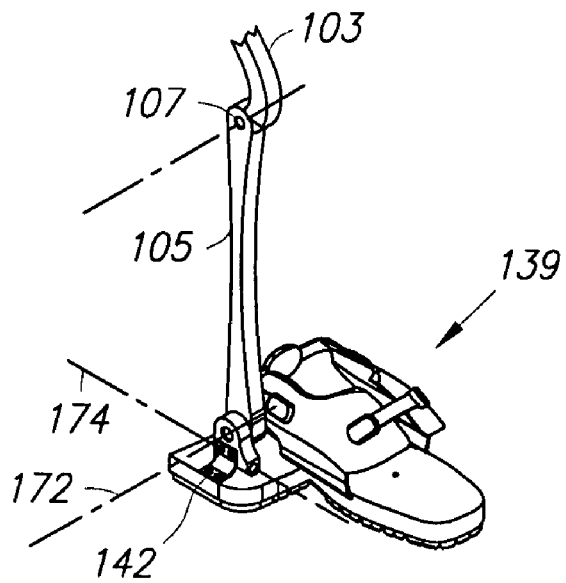
FIG. 18 is a perspective drawing in accordance with an embodiment of the exoskeleton foot.

In some embodiments, as shown in FIG. 18, exoskeleton feet 139 and 140 rotate about two ankle abduction-adduction axes 174 relative to shank links 105 and 106. FIG. 18 shows an embodiment of this type of exoskeleton where ankle abduction-adduction axis 174 is generally parallel to the abduction-adduction axis in the human ankle. In some embodiments each leg support further comprises at least one ankle abduction-adduction resilient element 142 resisting the rotation of exoskeleton foot 139 about ankle abduction-adduction axis 174.

Figure 19:
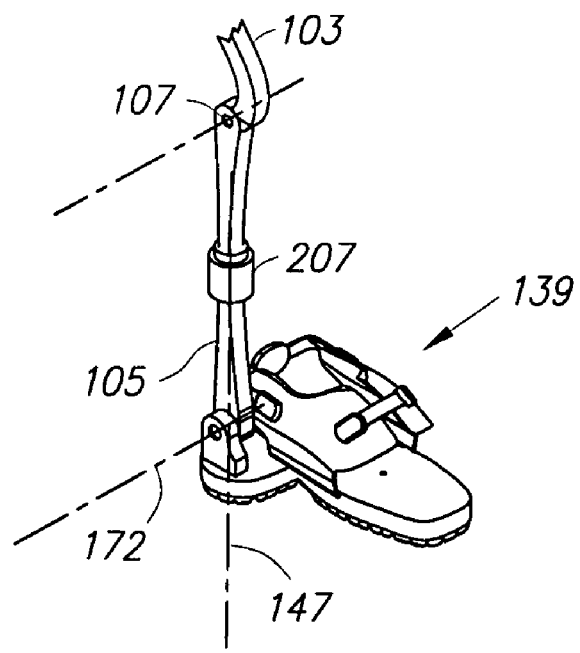
FIG. 19 is a perspective drawing in accordance with an embodiment of the exoskeleton foot.

In some embodiments, as shown in FIG. 19, exoskeleton feet 139 and 140 rotate about two ankle rotation axes 147 and 148 relative to shank links 105 and 106. In some cases, this is accomplished using a shank rotation joint 207 which functions similar to leg rotation joint 127. FIG. 19 shows an embodiment of this type of exoskeleton where ankle rotation axis 147 is generally parallel to the rotation axis in the human ankle. In some embodiments, resilient elements can be included in the ankle to resist the rotation of the exoskeleton foot 139 about ankle rotation axis 147.

Figure 22:
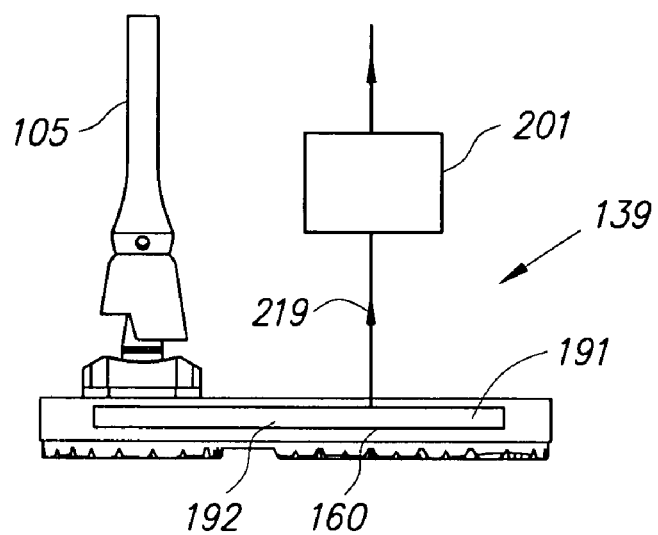
FIG. 22 is a drawing in accordance with an embodiment of the exoskeleton foot.

In some embodiments, as shown in FIG. 22, foot sensors 160 are integrated into exoskeleton feet 139 and 140. In some embodiments, as shown in FIG. 22, foot sensor 160 is a pressure sensor measuring the pressure in a media 191 trapped in a foot sensor cavity 192 inside exoskeleton foot 139. FIG. 16 shows an embodiment where a tube is used as a foot sensor cavity 192. Pressure sensor 160 measures the pressure in a media 191 trapped in a foot sensor cavity 192. In some cases, the stance signal 219 may take the form of the media 191 itself ported in a small tube from the cavity 192 to signal processor 159.

Figure 23:
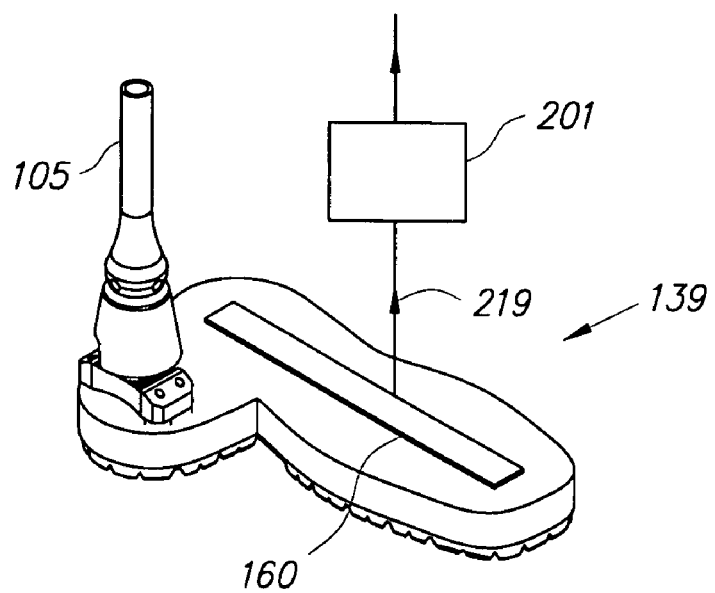
FIG. 23 is a drawing in accordance with an embodiment of the exoskeleton foot.
Figure 24:
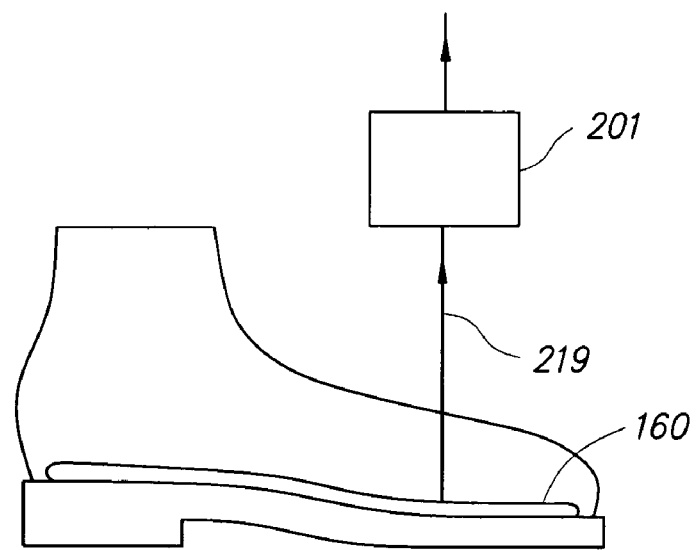
FIG. 24 is a drawing in accordance with an embodiment of the exoskeleton foot.
Figure 25:
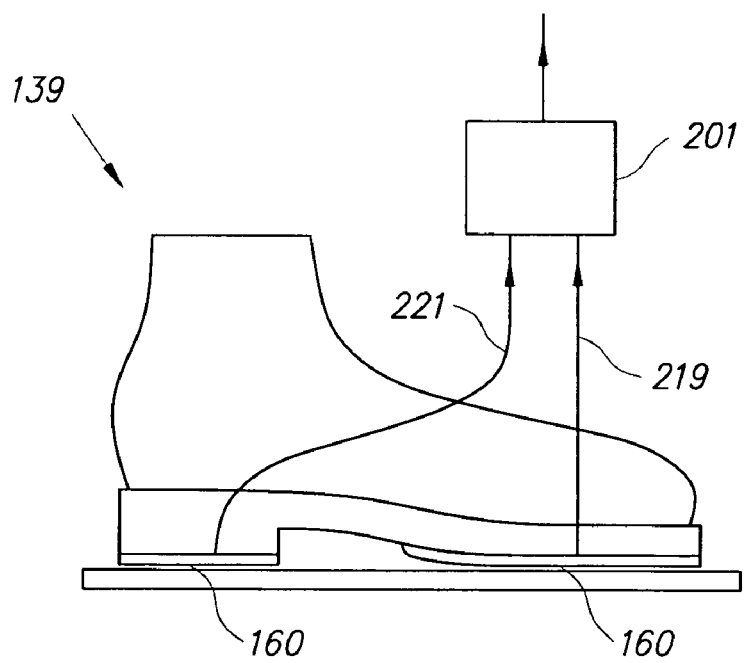
FIG. 25 is a drawing in accordance with an embodiment of the exoskeleton foot.
Figure 26:
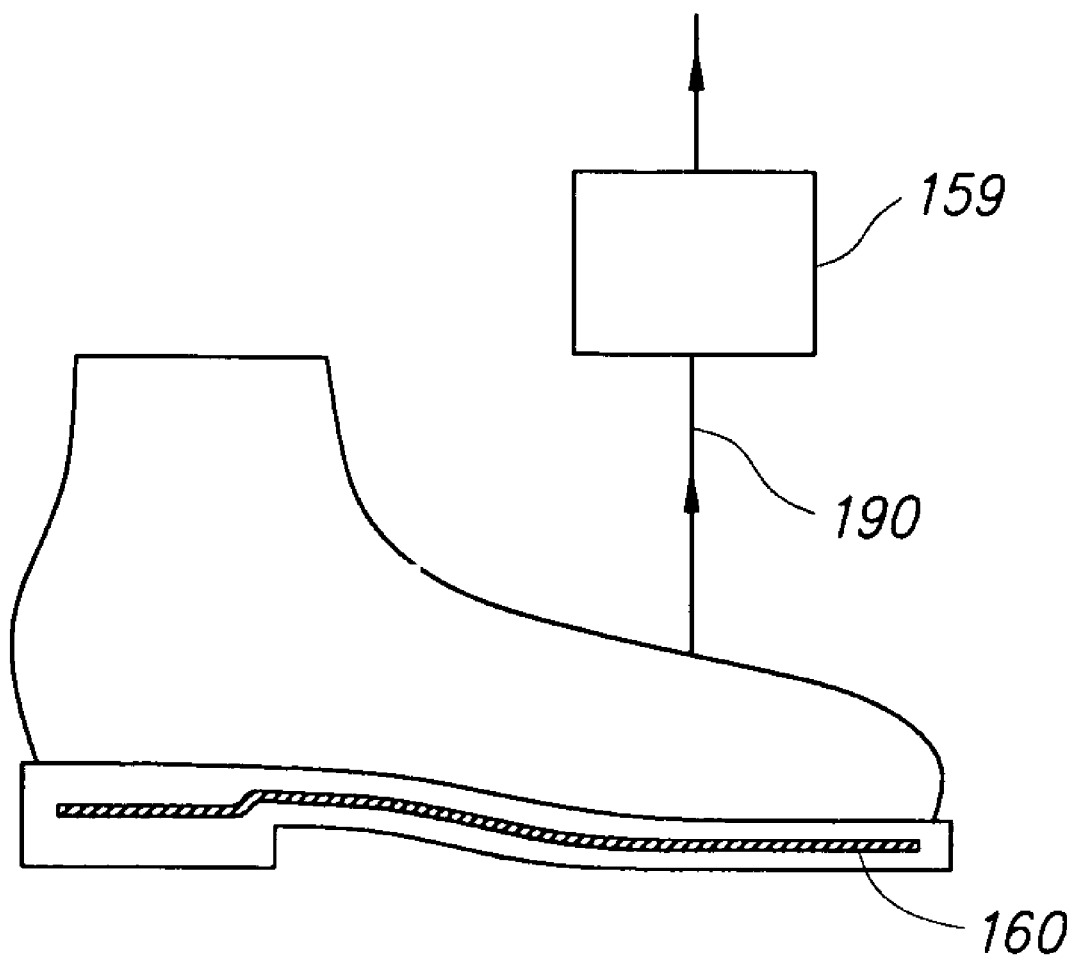
FIG. 26 is a drawing in accordance with an embodiment of the exoskeleton foot.

FIG. 23 shows another embodiment wherein foot sensor 160 is a force sensor connectable to exoskeleton foot 139. In some embodiments, as shown in FIG. 24, foot sensor 160 is located inside the human shoe like an insole and its output signal represents the force on the bottom of the human foot. This type would be particularly useful in embodiments of the invention such as those shown in FIG. 14 or 15. In some embodiments, as shown in FIG. 25, foot sensor 160 is connected to the bottom of the human shoe and senses the force on the bottom of the human foot. In some embodiments, as shown in FIG. 26, foot sensor 160 is located inside the human shoe sole and senses the force on the bottom of the human foot.

Foot sensor 160 comprises any sensor or combination of sensors capable of performing the indicated functions. Examples of foot sensor 160 include, without limitation, force sensors, strain-gage based force sensors, piezoelectric force sensors, force sensing resistors, pressure sensors, switches, tape switches and combinations thereof. In some embodiments foot sensor 160 is a switch that represents the existence of a force greater than some threshold force on the bottom of the foot of person 187.

Figure 27:
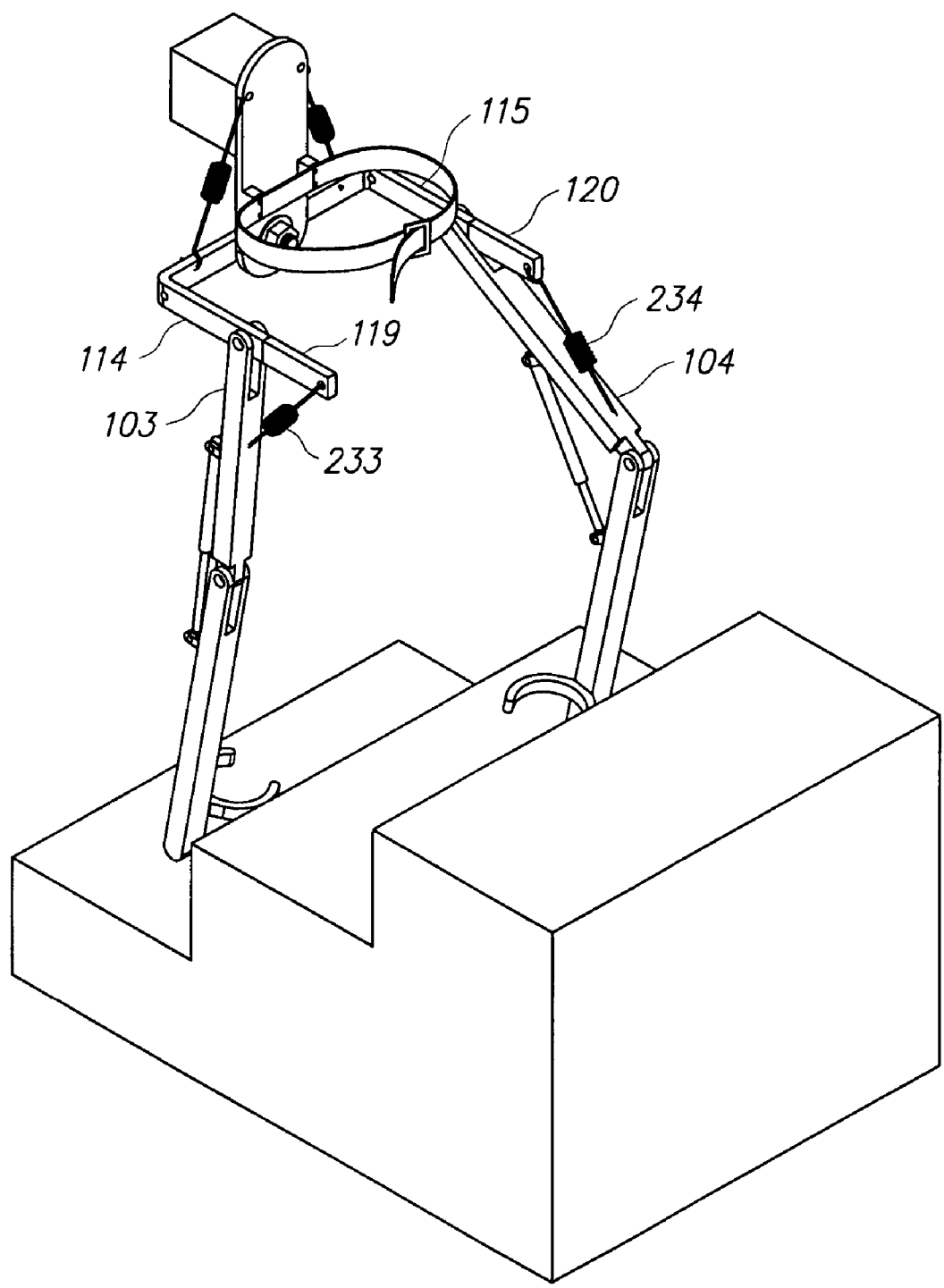
FIG. 27 is a perspective drawing in accordance with an embodiment of the invention.

In some embodiments lower extremity exoskeleton 100 further includes two compliant elements connecting thigh links 103 and 104 to exoskeleton trunk 109 assisting the operator in swinging the leg forward. This allows the operator to swing the thigh links forwardly with less effort. FIG. 27 shows an embodiment of the invention where tensile spring 233 connects thigh link 103 to hip link 114 via extension frame 119. Similarly tensile spring 234 connects thigh link 104 to hip link 115 via extension frame 120.

Figure 21:
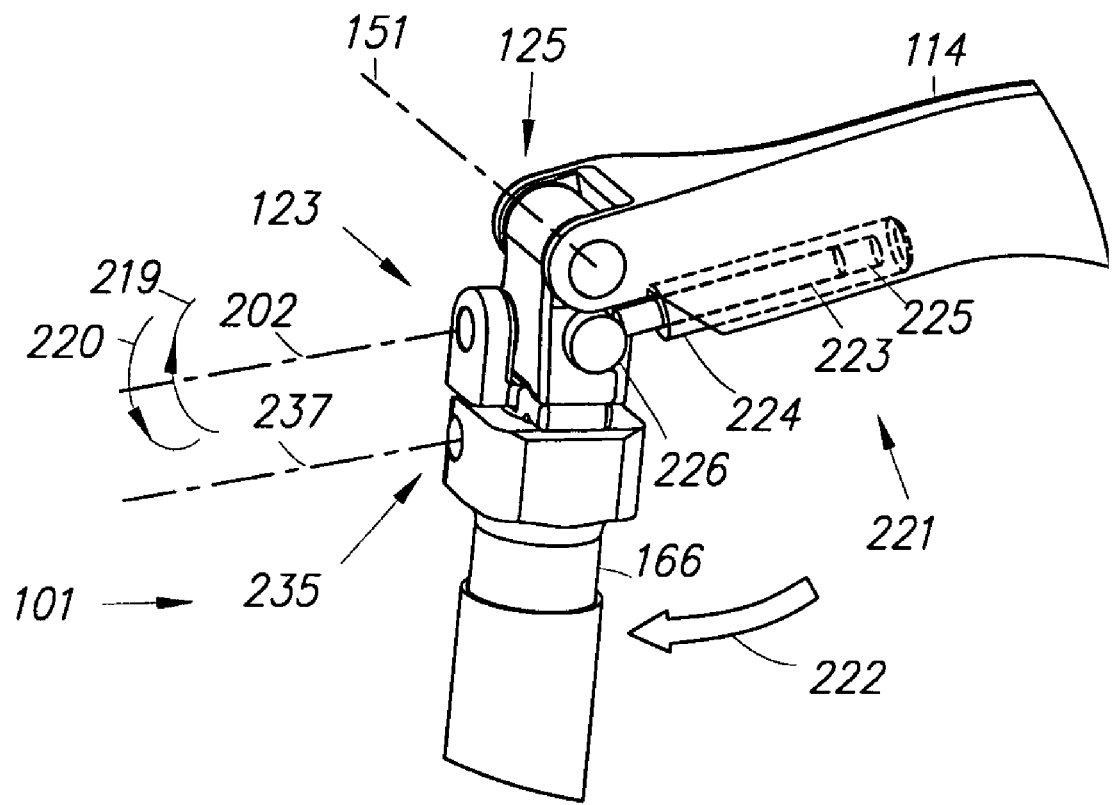
FIG. 21 is a perspective drawing in accordance with an embodiment of the invention.
Figure 36:
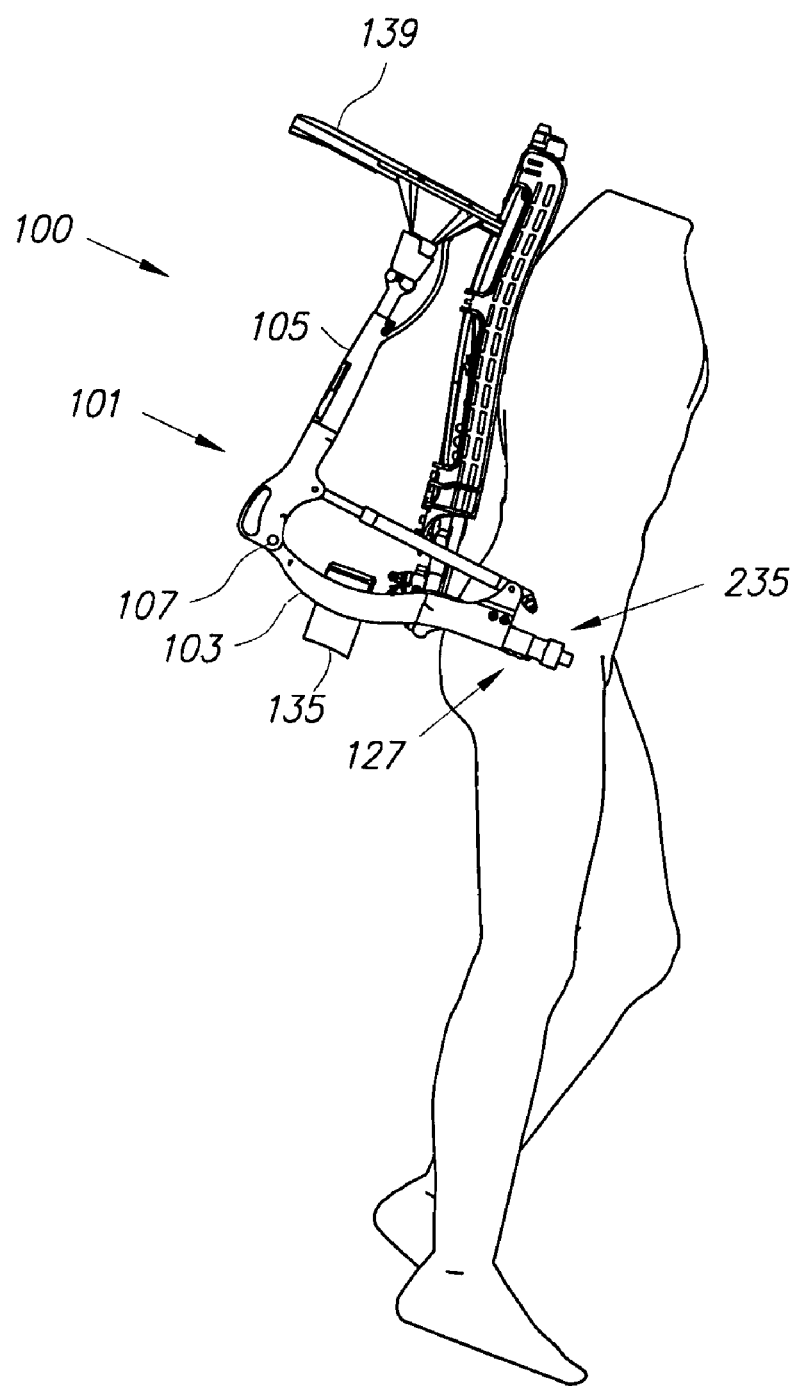
FIG. 36 is a drawing representing an embodiment of the exoskeleton stowed in a vertical position when the exoskeleton is not in use but needs to be carried.

Also shown in FIG. 21 is an additional thigh abduction-adduction joint 235 which is included in order to allow the leg to be stowed in a vertical position when the exoskeleton is not in use but needs to be carried. Leg support 101 can abduct along axis 237. This may be desirable if the operator no longer has a very heavy load to carry but needs to transport lower extremity exoskeleton 100. In that case, the operator may unstrap the exoskeleton's right leg support 101 and swing the leg outward from his or her body until the right exoskeleton foot 139 is in the air over the operator's head. Then by bending the right knee joint 107 and/or rotating the right leg rotation joint 127, the leg can be positioned such that it stows behind the operator as shown in FIG. 36. This is possible because the right thigh abduction-adduction joint 123 and the additional right thigh abduction-adduction joint 235 each allow for a rotation of approximately ninety degrees about the right thigh abduction-adduction axis 202 and the additional right thigh abduction-adduction axis 237 respectively. The total abduction possible therefore is over 180 degrees. This could be accomplished with one thigh abduction-adduction joint which has 180 degrees of travel, but designing such a joint would cause the designer to move the pivot point of the joint outward from the operator a great deal which would result in a wider exoskeleton design. This is undesirable but is a viable alternative design.

Although various exemplary embodiments have been described, it will be appreciated by persons skilled in the art that numerous variations and/or modifications may be made to the described device as specifically shown here without departing from the spirit or scope of that broader disclosure. The various examples are, therefore, to be considered in all respects as illustrative and not restrictive.

The invention claimed is:

1. A lower extremity exoskeleton, configurable to be coupled to a person, said lower extremity exoskeleton comprising:
   two leg supports configurable to be coupled to said person's lower limbs and configured to rest on the ground during their stance phases alongside said person's feet resting on the ground, wherein each said leg support comprises a thigh link and a shank link, and said two leg supports, during their stance phases, transfer forces from their shank links to the ground;

two knee joints, each configured to allow flexion and extension between the respective shank link and the respective thigh link; and an exoskeleton trunk configurable to be coupled to said person's upper body, rotatably connectable to said thigh links of said leg supports allowing for flexion and extension between said leg supports and said exoskeleton trunk;

two torque generators coupled to said knee joints; and a power unit, capable of providing power, coupled to said torque generators, wherein the power unit is configured to operate in at least two modes for each torque generator, with said power unit including a power injecting subcomponent capable of injecting power to the torque generator, and a power dissipating subcomponent capable of dissipating power from the torque generator, wherein:

when said power unit operates in its first mode with respect to one of said torque generators, said power unit injects power into the one of said torque generators to extend a respective knee angle defined between the respective shank link and respective thigh link, and when said power unit operates in its second mode with respect to the one of said torque generators, the energy required for said flexion and extension between the respective shank link and the respective thigh link of said corresponding leg support over a cyclic knee motion is provided by said person but said power unit causes the one of said torque generators to resist flexion.

2. The device of claim 1 wherein said power unit further operates in a third mode with respect to a torque generator, wherein:

when said power unit operates in said third mode with respect to one of said torque generators, the energy required for said flexion and extension between the shank link and the respective thigh link of said corresponding leg support over a cyclic knee motion is provided by said person, and wherein the torque generator's resistance to knee flexion and extension is minimized.

3. The device of claim 1 wherein the energy required for flexion and extension movement between a thigh link and said exoskeleton trunk over a cyclic hip motion is provided by said person.

4. The lower extremity exoskeleton of claim 2 wherein said lower extremity exoskeleton comprises at least one foot sensor per said leg support which produces a stance signal representing force on the bottom of each person's foot, and wherein said power unit controls said torque generators as a function of said stance signals.

5. The lower extremity exoskeleton of claim 4 wherein said lower extremity exoskeleton further comprises at least one angle sensor per said leg support which produces an angle signal representing the knee angle, wherein said power unit controls said torque generators as a function of said angle signals.

6. The device of claim 5 wherein said power unit operates in said first mode with respect to one of said torque generators when said corresponding stance signal indicates the presence of a force on the bottom of corresponding human foot and said corresponding angle sensor detects that said corresponding leg support is either bent or postured to climb stairs or a slope.

7. The device of claim 5 wherein said power unit operates in said first mode with respect to one of said torque generators, when said corresponding stance signal indicates the presence of a force on the bottom of corresponding human foot and said corresponding angle signal indicates that said corresponding leg support is in a position from which to extend said knee.

8. The device of claim 5 wherein said power unit operates in said second mode with respect to one of said torque generators, when said corresponding stance signal indicates the presence of a force on the bottom of corresponding human foot and said corresponding angle signal indicates that said corresponding leg support is neither bent nor postured to climb stairs or a slope.

9. The device of claim 4 wherein said power unit operates in said third mode with respect to one of said torque generators when said corresponding stance signal detects that a leg support is in a swing phase.

10. The device of claim 1 wherein each said torque generator comprises a hydraulic torque generator, and wherein said power unit, capable of providing hydraulic power, includes a hydraulic circuitry connectable to said hydraulic torque generators, wherein said hydraulic circuitry is configured to control said hydraulic torque generators by modulating the hydraulic fluid flow to and from said hydraulic torque generators.

11. The device of claim 10 wherein said hydraulic torque generator is a hydraulic piston-cylinder.

12. The device of claim 10 wherein said hydraulic torque generator is a rotary hydraulic vane type torque generator.

13. The device of claim 10 wherein said hydraulic circuitry comprises a hydraulic pump coupled to a motor, wherein when said power unit operates in said first mode with respect to one of said torque generators, said hydraulic pump injects hydraulic fluid into that torque generator causing knee joint of said corresponding leg support to extend.

14. The device of claim 10 wherein said power injecting subcomponent includes a hydraulic pump coupled to a motor, wherein when said power unit operates in said first mode with respect to one of said torque generators, said a pump isolating valve connects said hydraulic pump to the one of said torque generators.

15. The device of claim 10 wherein said power dissipating subcomponent includes an actuated flow restricting valve, wherein when said power unit operates in said second mode with respect to one of said torque generators, said actuated flow restricting valve restricts the fluid flow from the one of said torque generators.

16. The device of claim 15 wherein when said power unit operates in a third mode with respect to one of said torque generators, said actuated flow restricting valve opens and allows for minimum resistance hydraulic fluid flow between that torque generator and a source of hydraulic fluid.

17. The device of claim 13 wherein said motor is an electric motor, wherein when said power unit operates in a power regeneration mode with respect to one of said torque generators, that torque generator injects hydraulic fluid into said hydraulic pump, which then acts as a hydraulic motor, causing said electric motor, which then acts as an electric generator, to generate electricity.

18. The device of claim 10 wherein said hydraulic circuitry further comprises a hydraulic check valve connecting a source of hydraulic fluid to said torque generator allowing for free extension of said knee when said power units operates in said first and second modes.

19. The device of claim 15 wherein said hydraulic circuitry further comprises a three-way valve, wherein when said power unit is operating in said first mode with respect to one of said torque generators, said three-way valve connects that hydraulic torque generator to said hydraulic pump; and when said power unit is operating in the second mode said three-way valve connects that hydraulic torque generator to said actuated flow restricting valve.

20. The device of claim 5 wherein said power unit further comprises a signal processor capable of controlling said power unit.

21. The device of claim 20 wherein said signal processor comprises an element or combination of elements selected from a group consisting of analog devices; analog computation modules; digital devices including, without limitation, small-, medium-, and large-scale integrated circuits, application specific integrated circuits, programmable gate arrays, and programmable logic arrays; and digital computation modules including, without limitation, microcomputers, microprocessors, microcontrollers, and programmable logic controllers.

22. The device of claim 20 wherein signal processor comprises an element or combination of elements selected from a group consisting of electromechanical relays or MOSFET switches.

23. The device of claim 20 wherein signal processor generates command signals for said hydraulic circuitry from said stance signals, said angle signal, or combination of stance signals and angle signals.

24. The device of claim 1 wherein said exoskeleton trunk further allows for rotation of each said leg support about an abduction-adduction axis generally parallel to ground.

25. The device of claim 1 wherein said exoskeleton trunk further comprises two hip links rotatably connectable to said respective thigh links to allow for said flexion and extension of said support legs relative to said exoskeleton trunk; wherein said hip links are rotatably connected to each other to allow for abduction of leg supports.

26. The device of claim 1 wherein said exoskeleton trunk further comprises two hip links rotatably connectable to said respective thigh links to allow for said flexion and extension of said support legs relative to said exoskeleton trunk; wherein said hip links are rotatably connected to each other to allow for adduction of leg supports.

27. The device of claim 1 wherein said exoskeleton trunk is configured to hold a rear load behind said person when said exoskeleton trunk is coupled to said person's upper body.

28. The device of claim 1 wherein said exoskeleton trunk further comprises an extension frame configured to hold a front load in front of said person when said exoskeleton trunk is coupled to said person's upper body.

29. The device of claim 25 wherein said exoskeleton trunk further comprises a hip resilient element configured to apply a torque between said hip links.

30. The device of claim 26 wherein said exoskeleton trunk further comprises a hip resilient element configured to apply a torque between said hip links.

31. The devices of claim 29 or 30 wherein said hip resilient element comprises an elastic element or combination of elastic elements selected from a group consisting of extension spring, compression spring, leaf spring, air spring, gas spring, rubber, elastomer, surgical tube, and bungee cord.

32. The device of claim 25 wherein said exoskeleton trunk further comprises a hip abduction stop to limit the abduction of said hip links with respect to each other.

33. The device of claim 1 wherein said exoskeleton trunk further comprises two hip links rotatably connectable to said respective thigh links allowing for said flexion and extension of said support legs; wherein said hip links are compliantly connected to each other allowing for adduction of leg supports.

34. The device of claim 1 wherein said exoskeleton trunk further comprises two hip links rotatably connectable to said respective thigh links allowing for said flexion and extension of said support legs; wherein said hip links are compliantly connected to each other allowing for abduction of leg supports.

35. The device of claim 1 wherein said exoskeleton trunk further comprises a connecting bracket configured to transfer weight of a load to said exoskeleton trunk.

36. The device of claim 35 wherein said exoskeleton trunk further comprises two hip links rotatably connectable to said respective thigh links to allow for said flexion and extension of said support legs relative to said exoskeleton trunk; wherein said hip links are rotatably connected to said connecting bracket via two hip abduction-adduction joints to allow for rotational motion of said leg supports about two abduction-adduction axes.

37. The device of claim 36 wherein said abduction-adduction axes are generally parallel to each other.

38. The device of claim 36 wherein said abduction-adduction joints coincide on each other.

39. The device of claim 35 wherein said load is an object selected from a group consisting of backpack, baby carrier, food containers, sacks, water jugs, tool boxes, barrels, ammunition, weaponry, bedding, first aid supplies, golf bags, mail bags, camera, leaf blower, compressor, electromechanical machineries and combinations thereof.

40. The device of claim 35 wherein said load is another person.

41. The device of claim 36 wherein said exoskeleton trunk further comprises hip abduction-adduction resilient elements configured to apply torques between said hip links and said connecting bracket.

42. The device of claim 41 wherein said hip abduction-adduction resilient elements, each comprises an elastic element or combination of elastic elements selected from a group consisting of extension spring, compression spring, leaf spring, air spring, gas spring, rubber, elastomer, surgical tube, and bungee cord.

43. The device of claim 35 wherein said connecting bracket further comprises an extension frame configured to hold said load in front of said person when said exoskeleton trunk is coupled to said person's upper body.

44. The device of claim 35 wherein said exoskeleton trunk comprises a human interface device capable of coupling said person's upper body to lower extremity exoskeleton.

45. The device of claim 44 wherein said human interface device is capable of transferring a portion of the weight of said person to said exoskeleton trunk.

46. The device of claim 44 wherein said human interface device comprises an element or combination of elements selected from a group consisting of vests, belts, straps, shoulder straps, chest straps, body cast, harness, and waist belts.

47. The device of claim 34 wherein said exoskeleton trunk further comprises two hip links rotatably connectable to said respective thigh links allowing for said flexion and extension of said support legs wherein said hip links are compliantly connected to each other allowing for adduction of leg supports.

48. The device of claim 1 wherein said thigh link of each said leg support further includes a thigh abduction-adduction joint configured to allow abduction of said perspective leg support.

49. The device of claim 48 wherein said abduction-adduction joints are generally located below said hip flexion-extension joints.

50. The device of claim 1 wherein said thigh of each said leg support further includes a thigh abduction-adduction joint configured to allow adduction of said leg support.

51. The device of claim 50 wherein said abduction-abduction joints are generally located below said hip flexion-extension joints.

52. The device of claim 1 wherein each said leg support further includes a leg rotation joint configured to allow rotation of said leg support.

53. The device of claim 52 wherein said leg rotation joints are generally located above said knee flexion-extension joints.

54. The device of claim 52 wherein said leg rotation joints further comprise a leg rotation resilient element that provides a restoring torque which generally restores said leg support back to a neutral position.

55. The device of claim 1 wherein said thigh link of each said leg support further includes a compression-elongation mechanism configured to allow a change in the distance between said hip flexion-extension joint and said knee flexion-extension joint.

56. The device of claim 55 wherein said compression-elongation mechanism comprises a leg compression-elongation resilient element that provides a restoring force which generally restores said leg support back to a neutral configuration.

57. The device of claim 1 further comprising two swing resilient elements configured to apply torque between said thigh links and said exoskeleton trunk.

58. The device of claim 1 wherein said thigh links include thigh holding devices configured to allow said person to couple to said leg supports.

59. The device claim 58 wherein each said thigh holding device comprises an element or combination of elements selected from a group consisting of strap, bar, c-shape brackets, body cast and elastomers.

60. The device of claim 1 wherein said shank links include shank holding devices configured to allow said person to couple to said leg supports.

61. The device claim 60 wherein each said shank holding device comprises an element or combination of elements selected from a group consisting of strap, bar, c-shape brackets, body cast and elastomers.

62. The device of claim 1 wherein each said leg support further comprises an exoskeleton foot configured to be coupled to respective said person's foot and coupled to respective said shank link to allow the transfer of forces from said shank link to the ground.

63. The device of claim 1 wherein each said leg support further comprises an exoskeleton foot coupled to respective said shank link and configured to be coupled to the bottom of the said respective person's shoe to allow the transfer of forces from said shank link to the ground.

64. The device of claim 62 wherein each said exoskeleton foot further comprises a shoe wearable by said person to allow said exoskeleton foot to couple said person's foot.

65. The device of claim 62 wherein each said exoskeleton foot further comprises an exoskeleton insole insertable inside said person's shoe to allow said exoskeleton foot to couple said person's foot.

66. The device of claim 1 wherein each said leg support further comprises an exoskeleton foot configured to be coupled to respective said person's foot and compliantly coupled to respective said shank link to allow the transfer of forces from said shank link to the ground.

67. The device of claim 1 wherein each said leg support further comprises an exoskeleton foot configured to be coupled to respective said person's foot and rotatably coupled to respective said shank link to allow the transfer of forces from said shank link to the ground; said exoskeleton foot rotates about an ankle plantar-dorsi flexion axis generally parallel to plantar-dorsi flexion axis in the human ankle.

68. The device of claim 67 wherein each said leg support further comprises at least one ankle plantar-dorsi flexion resilient element resisting the rotation of respective said exoskeleton foot about said ankle plantar-dorsi flexion axis.

69. The device of claim 1 wherein each said leg support further comprises an exoskeleton foot configured to be coupled to respective said person's foot and rotatably coupled to respective said shank link to allow the transfer of forces from said shank link to the ground; said exoskeleton foot rotates about an ankle abduction-adduction axis generally parallel to abduction-adduction axis in the human ankle.

70. The device of claim 69 wherein said each leg support further comprises at least one ankle abduction-adduction resilient element to resist the rotation of respective said exoskeleton foot about said ankle abduction-adduction axis.

71. The device of claim 1 wherein each said leg support further comprises an exoskeleton foot configured to be coupled to respective said person's foot and rotatably coupled to respective said shank link to allow the transfer of forces from said shank link to the ground; said exoskeleton foot rotates about an ankle rotation axis generally parallel to rotation axis in the human ankle.

72. The device of claim 71 wherein each said leg support further comprises at least one resilient element to resist the rotation of respective said exoskeleton foot about said ankle rotation axis.

73. A method of operating a lower extremity exoskeleton, said lower extremity exoskeleton comprising:
two leg supports configurable to be coupled to a person's lower limbs and configured to rest on the ground during their stance phases alongside a person's feet, wherein each said leg support comprises a thigh link and a shank link, and said two leg supports, during their stance phases, transfer forces from their shank links to the ground; two knee joints, each configured to allow flexion and extension between the respective shank link and the respective thigh link; and an exoskeleton trunk configurable to be coupled to said person's upper body, rotatably connectable to said thigh links of said leg supports allowing for flexion and extension between said leg supports and said exoskeleton trunk; and two torque generators coupled to each said knee joints;
said method comprising:
coupling a person to said exoskeleton;
automatically operating a power unit to allow the flexion of said respective knee joint during a swing phase;
automatically operating the power unit to cease injecting power into a respective torque generator and resist flexion of said respective knee joint during the stance phase of the respective leg support when a signal indicates that said leg support is not posed to climb stairs or a slope; and
automatically operating the power unit to resist flexion of said respective knee joint and inject power into the respective torque generator during the stance phase to extend a respective knee angle when a signal indicates that said leg support is posed to climb stairs or a slope.

74. A method of stowing an exoskeleton configurable to be coupled to a person's upper body including an exoskeleton leg rotatably coupled to a trunk of the exoskeleton at a thigh joint, the exoskeleton leg having a thigh link connected to a shank link, and a knee joint allowing flexion and extension between the thigh link and the shank link, said method comprising: abducting the exoskeleton leg about the knee joint and the thigh joint to rotate the thigh link and the shank link such that the exoskeleton leg is rotated a full 180 degrees with respect to the trunk of the exoskeleton to a stowed position.

75. A system to operate an artificial knee disposed between a thigh link and a shank link, wherein a knee angle is defined between the thigh link and the shank link, and wherein the thigh link and the shank link comprise a leg support, the system comprising:
   a hydraulic actuator coupled to said artificial knee; and
   a power unit coupled to the hydraulic actuator, wherein said power unit is configured to operate automatically in at least one of two modes, wherein:
   when said power unit operates in its first mode with respect to said hydraulic actuator, said power unit injects power into the hydraulic actuator through a power injecting subcomponent to extend said knee angle; and
   when said power unit operates in its second mode with respect to said hydraulic actuator, the energy required for said flexion and extension between the shank link and the respective thigh link of said artificial knee over a cyclic knee motion is provided by a person but said power unit causes the torque generator to resist flexion through a power dissipating subcomponent when signals indicate that the leg support rests on the ground, alongside a person's foot, in a stance phase.

76. A lower extremity exoskeleton, configurable to be coupled to a person, said lower extremity exoskeleton comprising:
   two leg supports configurable to be coupled to a person's lower limbs and configured to rest on the ground during their stance phases alongside a person's feet resting on the ground, wherein each said leg support comprises a thigh link and a shank link, and said two leg supports, during their stance phases, transfer forces from their shank links to the ground;
   two knee joints, each configured to allow flexion and extension between the respective shank link and the respective thigh link;
   an exoskeleton trunk configurable to be coupled to a person's upper body, rotatably connectable to said thigh links of said leg supports allowing for flexion and extension between said leg supports and said exoskeleton trunk;
   two torque generators coupled to said knee joints; and
   a power unit configured to operate automatically in one of at least two modes, the power unit comprising a hydraulic circuit connecting the power unit and the two torque generators, a hydraulic pump coupled to a motor, and an actuated flow restricting valve between the power unit and the two torque generators, wherein:
   when said power unit operates in a first mode with respect to one of said torque generators, said hydraulic pump injects hydraulic fluid into the one of said torque generators to cause said knee joint of said corresponding leg support to extend and,
   when said power unit operates in a second mode with respect to the one of said torque generators, the hydraulic pump does not inject hydraulic fluid into the one of said torque generators, the energy required for said flexion and extension between the respective shank link and the respective thigh link of said corresponding leg support over a cyclic knee motion is provided by said person and said actuated flow restricting valve restricts the hydraulic fluid flow from the one of said torque generators to the hydraulic circuit.

77. The device of claim 76 wherein when said power unit operates in a third mode with respect to the one of said torque generators, the hydraulic pump does not inject hydraulic fluid into the one of said torque generators, the energy required for said flexion and extension between the shank link and the respective thigh link of said corresponding leg support over a cyclic knee motion is provided by said person and said actuated flow restricting valve opens and allows for minimum resistance hydraulic fluid flow between the one of the torque generators and a source of hydraulic fluid.

78. The device of claim 76 wherein said motor is an electric motor, wherein when said power unit operates in a power regeneration mode with respect to one of said torque generators, that torque generator injects hydraulic fluid into said hydraulic pump, which then acts as a hydraulic motor, causing said electric motor, which then acts as an electric generator, to generate electricity.

79. The method of claim 73, further comprising: coupling an object to said exoskeleton.

* * * * *